(12) United States Patent
Goronzy et al.

(10) Patent No.: US 6,555,320 B1
(45) Date of Patent: Apr. 29, 2003

(54) METHODS AND MATERIALS FOR EVALUATING RHEUMATOID ARTHRITIS

(75) Inventors: Jorg J. Goronzy, Rochester, MN (US); Cornelia M. Weyand, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 09/387,467

(22) Filed: Sep. 1, 1999

Related U.S. Application Data
(60) Provisional application No. 60/098,718, filed on Sep. 1, 1998.

(51) Int. Cl.$^7$ .................. G01N 33/53; A61K 39/00; A61K 39/395

(52) U.S. Cl. .................. 435/7.1; 424/130.1; 424/140.1; 424/143.1; 424/145.1; 530/388.22; 530/388.23; 530/389.2; 530/391.1

(58) Field of Search .................. 424/145.1, 140.1, 424/143.1, 130.1; 435/975, 7.1; 530/388.22, 388.23, 389.2, 391.1

(56) References Cited

U.S. PATENT DOCUMENTS 5,292,636 A * 3/1994 Kung et al. .................. 435/5

OTHER PUBLICATIONS

Klimiuk PA et al. 1997. Am J Pathology. vol. 151, pp. 1311–1319. Tsiissue cytokine patterns distinguish variants of rheumatoid synovitis.*
Clin Exp Rheumatol Mar.–Apr. 1996; 14(2):155–162. Schlaak JF, Pfers I, et al. Different cytokine profiles in the synovial fluid of patients with osteoarthritis, rheumatoid arthritis and seronegative spodylarthropathies.*
Stratagene catalog, 1988.*
Abbas AK et al., "Functional diversity of helper T lymphocytes," *Nature* 383:787–793 (1996).
Abril A et al., "Genetic factors influence the emergence of CD28 deficient CD4+T cells and may represent novel disease risk genes for rheumatoid arthritis," *Arthritis Rheum.*, 1998, 40:762.
Albani S, et al., "A multistep molecular mimicry hypothesis for the pathogenesis of rheumatoid arthritis," *Immunol Today* 17:466–470 (1996).
Albani S, et al., "Positive selection in autoimmunity: abnormal immune responses to a bacterial dnaJ antigenic determinant in patients with early rheumatoid arthritis," *Nat Med* 1:448–452 (1995).
Arnett FC et al., "The American Rheumatism Association 1987 revised criteria for the classification of rheumatoid arthritism," *Arthritis Rheum.* 31:315–324 (1988).

Barnes PF et al., "Local production of tumor necrosis factor and IFN–gamma in tuberculous pleuritis," *J Immunol* 145:149–154 (1990).
Boros DL, "The role of cytokines in the formation of the schistosome egg granuloma," *Immunobiology* 91:441–450 (1994).
Boros DL, "Granulomatous inflammations," *Prog Allergy* 24:183–267 (1978).
Brack A et al., "Glucocorticoid–mediated repression of cytokine gene transcription in human arteritis–SCID chimeras," *J Clin Invest* 99:2842–2850 (1997).
Brown JH, et al., "Three–dimensional structure of the human class II histocompatibility antigen HLA–DR1," *Nature* 364:33–39 (1993).
Burmester GR et al., "Mononuclear phagocytes and rheumatoid synovitis. Mastermind or workhorse in arthritis," *Arthritis Rheum* 40:5–18 (1997).
Chapman A, et al., "CD11b+CD28–CD4+ human T cells: activation requirements and association with HLA–DR alleles," *J Immunol* 157:4771–4780 (1996).
Chensue SW et al., "Evolving T cell responses in murine schistosomiasis. Th2 cells mediate secondary granulomatous hypersensitivity and are regulated by CD8+ T cells in vivo," *J Immunol* 151:1391–1400 (1993).
Chensue SE et al., "Role of IL–4 and IFN–gamma in *Schistosoma mansoni* egg–induced hypersensitivity granuloma formation. Orchestration, relative contribution, and relationship to macrophage function," *J Immunol* 148:900–906 (1992).
Cornelis F, et al., "Association of rheumatoid arthritis with an amino acid allelic vartiation of the T cell receptor," *Arthritis Rheum* 40:1387–1390 (1997).
DerSimonian H, et al., "Clonal V Alpha 12.1+ T cell expansions in the peripheral blood of rheumatoid arthritis patients," *J Exp Med* 177:1623–1631 (1993).
Dessen A, et al., "X–ray crystal structure of HLA–DR4 (DRA*0101, DRB1*0401) complexed with a peptide from human collagen II," *Immunity* 7:473–481 (1997).
Feldmann M et al., "Rheumatoid arthritis," *Cell* 85:307–310 (1996).
Finkelman FD, "Relationships among antigen presentation, cytokines, immune deviation, and autoimmune disease," *J Exp Med* 182:279–282 (1995).
Firestein GS et al., "How important are T cells in chronic rheumatoid synovitis?," *Arthritis Rheum* 33:768–773 (1990).

(List continued on next page.)

Primary Examiner—Hankyel T. Park
Assistant Examiner—Stacy S. Brown
(74) Attorney, Agent, or Firm—Fish & Richardson, P.C., P.A.

(57) ABSTRACT

The invention provides methods and materials for diagnosing a rheumatoid arthritis condition in a patient. Specifically, the invention provides methods and materials for classifying a rheumatoid arthritis condition as diffuse, follicular, or granulomatous. In addition, the invention provides methods and materials for determining if an individual suffering from a rheumatoid arthritis condition will develop severe disease.

34 Claims, 6 Drawing Sheets

OTHER PUBLICATIONS

Fitzgerald JE, et al., "Analysis of clonal CD8+ T cell expansions in normal individuals and patients with rheumatoid arthritis," *J Immunol* 154:3538–3547 (1995).

Fox DA, "The role of T cells in the immunopathogenesis of rheumatoid arthritis: new perspectives," *Arthritis Rheum* 40:598–609 (1997).

Fu YX, et al., "Statistical tests of neutrality of mutations against population growth, hitchhiking and background selection," *J Exp Med* 181:915–925 (1991).

Gonzalez–Quintial R, et al., "Identification of clonally expanded T cells in rheumatoid arthritis using a sequence enrichment nuclease assay," *J Clin Invest* 97:1335–1343 (1996).

Goronzy JJ, et al., "Dominant clonotypes in the repertoire of peripheral CD4+ T cells in rheumatoid arthritis," *J Clin Invest* 94:2068–2076 (1994).

Goronzy JJ et al., "T cells in rheumatoid arthritis. Paradigms and facts," *Rheum Dis Clin North Am* 21:655–674 (1995).

Goronzy JJ, et al., "Vasculitis in rheumatoid arthritis," *Curr. Opin. Rheumatol.*, 1994, 6:290–294.

Gough A, et al., "Genetic typing of patients with inflammatory arthritis at presentation can be used to predict outcome," *Arthritis Rheum.*, 1994, 37:1166–1170.

Gregersen PK et al., "The shared epitope hypothesis. An approach to understanding the molecular genetics of susceptibility to rheumatoid arithritis," *Arthritis Rheum* 30:1205–1213 (1987).

Grzych JM et al., "Egg depositon is the major stimulus for the production of Th2 cytokines in murine schistosomiasis mansoni," *J Immunol* 146:1322–1327 (1991).

Hale LP et al. "Pathology of rheumatoid arthritis and associated disorders," Arthritis and Allied Conditions, edited by Koopman WJ. Baltimore, Williams & Wilkins, pp. 993–1016 (1997).

Hall FC, et al., "A linkage study across the T cell receptor A and T cell receptor B loci in families with rheumatoid arthritis," *Arthritis Rheum* 40:1798–1802 (1997).

Hammer J, et al., "Peptide binding specificity of HLA–DR4 molecules: correlation with rheumatoid arthritis association," *J Exp Med* 181:1847–1855 (1995).

Harris ED (ed); Rheumatoid Arthritis, Philadelphia, WB Saunders Co., pp. 3–212 (1997).

Heinzel FP et al., "Reciprocal expression of interferon gamma or interleukin 4 during the resolution or progression of murine leishmaniasis. Evidence for expansion of distinct helper T cell subsets," *J Exp Med* 169:59–72 (1989).

Hingorani R, et al., "Oligoclonality of V beta 3 TCR chains in the CD8+ T cell population of rheumatoid arthritis patients," *J Immunol* 156:852–858 (1996).

Hiraiwa A, et al., "Structural requirements for recognition of the HLA–Dw14 class II epitope: a key HLA determinant associated with rheumatoid arthritis," *Proc Natl Acad Sci USA* 87:8051–8055 (1990).

Isomaki P et al., "Interleukin–10 functions as an antiinflammatory cytokine in rheumatoid synovium," *Arthritis Rheum* 39:386–395 (1996).

Kelsoe G, "The germinal center: a crucible for lymphocyte selection," *Semin Immunol* 8:179–184 (1996).

Kindler V et al., "The inducing role of tumor necrosis factor in the development of bactericidal granulomas during BCG infection," *Cell* 56:731–740 (1989).

Klimiuk PA et al., "Tissue cytokine patterns distinguish variants of rheumatoid synovitis," *Am J Pathol* 151:1311–1319 (1997).

Kuhn R et al., "Generation and analysis of interleukin–4 deficient mice," *Science* 254:707–710 (1991).

Kurosaka M, et al., "Immunoelectron microscopic study of the distribution of T cell subsets in rheumatoid synovium," *J Exp Med* 158:1191–1210 (1983).

Lanchbury JS, et al., "Strong primary selection for the Dw4 subtype of DR4 accounts for the HLA–DQw7 association with Felty's syndrome," *Hum Immunol* 32:56–64 (1991).

Levy Y et al., "Interleukin–10 prevents spontaneous death of germinal center B cells by induction of the bcl–2 protein," *J Clin Invest* 93:424–428 (1994).

Lim A, et al., "Spread of clonal T–cell expansions in rheumatoid arthritis patients," *Hum Immunol* 48:77–83 (1996).

Lynn AH, et al., "Genetic epidemiology of rheumatoid arthritis," *Am J Hum Genet*, 1995, 57:150–159.

Martens PB, et al., "Expansion of unusual CD4+ T cells in severe rheumatoid arthritis," *Arthritis Rheum* 40(6):1106–1114 (1997).

McDaniel DO, et al., "Most African–American patients with rheumatoid arthritis do not have the rheumatoid antigenic determinant," *Ann Intern Med* 123:181–187 (1995).

Merrill JT, et al., "Adenosine A1 receptor promotion of multinucleated giant cell formation by human monocytes: a mechanism for methotrexate–induced nodulosis in rheumatoid arthritis," *Arthritis Rheum* 40:1308–1315 (1997).

Namekawa T, et al., "Functional subsets of CD4 T cells in rheumatoid synovitis," *Arthritis Rheum.* 41(12):2108–2116 (1998).

Nepom GT et al., "MHC class–II molecules and autoimmunity," *Annu Rev Immunol* 9:493–525 (1991).

Ollier WE et al., "Genetic epidemiology of rheumatoid disease," *BR Med Bull* 51:267–285 (1995).

Olsen NJ, et al., "Associations of HL–DR4 with rheumatoid factor and radiographic severity in rheumatoid arthritis," *Am J Med*, 84:257–264 (1988).

Orme IM et al., Cytokines secretion by CD4 T lymphocytes acquired in response to *Mycobacterium tuberculosis* infection, *J Immunol* 151:518–525 (1993).

Panayi GS et al., "The importance of the T cell in initiating and maintaining the chronic synovitis of rheumatoid arthritis," *Arthritis Rheum* 35:729–735 (1992).

Park W et al., "Co–stimulatory pathways controlling activation and peripheral tolerance of human CD4+CD28– T cells," *Eur J Immunol* 27:1082–1090 (1997).

Penzotti JE, et al. "Use of T cell receptor/HLA–DRB1*04 molecular modeling to predict site–specific interactions for the DR shared epitope associated with rheumatoid arthritis," *Arthritis Rheum* 40:1316–1326 (1997).

Perez L et al., "Terminal differentiation of spontaneous rheumatoid factor–secreting B cells from rheumatoid arthritis patients depends on endogenous interleukin–10," *Arthritis Rheum* 38:1771–1776 (1995).

Randen I et al., "The identification of germinal centres and follicular dendritic cell networks in rheumatoid synovial tissue," *Scan J Immunol* 41:481–486 (1995).

Rigby AS, et al., "Epistatic modeling in rheumatoid arthritis: an application of the Risch theory," *Genet Epidemiol*, (1993,) 10:311–320.

Risch N, et al., "The future of genetic studies of complex human diseases," *Science*, (1996) 273:1516–1517.

Rittner HL, et al., "Multiple mechanisms support oligoclonal T cell expansion in rheumatoid synovitis," *Mol Med* 3(7):452–465 (1997).

Roudier J, et al, "Susceptibility to rheumatoid arthritis maps to a T–cell epitope shared by the HLA–Dw4 DR beta–1 chain and the Epstein–Barr virus glycoprotein gp110," *Proc Natl Acad Sci USA* 86:5104–5108 (1989).

Salvat S, et al., "Tolerance to a self–peptide from the third hypervariable region of HLA DRB1*0401 in rheumatoid arthritis patients and normal subjects," *J Immunol* 153:5321–5329 (1994).

Schmidt D, et al., "CD4+ CD7– CD28– T cells are expanded in rheumatoid arthritis and are characterized by autoreactivity," *J Clin Invest* 97(9):2027–2037 (1996).

Schmidt D, et al., "The repertoire of CD4+ CD28– T cells in rheumatoid arthritis," *Mol Med*, (1996) 2:608–618.

Schroder et al., "Differentiation of B cells in the nonlymphoid tissue of the synovial membrane of patients with rheumatoid arthritis," *Proc Natl Acad Sci USA* 93:221–225 (1996).

Seder RA and Paul WE, "Acquisition of lymphokine–producing phenotype by CD4+ T cells," *Annu Rev Immunol* 12:635–673 (1994).

Seder RA et al., "Interleukin 12 acts directly on CD4+ T cells to enhance priming for interferon gamma production and diminishes interleukin 4 inhibition of such priming," *Proc Natl Acad Sci USA* 90:10188–10192 (1993).

Seder RA et al., "The presence of interleukin 4 during in vitro priming determines the lymphokine–producing potential of CD4+ T cells from T cell receptor transgenic mice," *J Exp Med* 176:1091–1098 (1992).

Simon AK et al., "Divergent T–cell cytokine patterns in inflammatory arthritis," *Proc Natl Acad Sci USA* 91:8562–8566, (1994).

Stastny P, et al., "CD4+ CD7– CD28– T cells are expanded in rheumatoid arthritis and are characterized by autoreactivity," *J Clin Invest* 97(9):2027–2037 (1996).

Stern LJ, et al., "Crystal structure of the human class II MHC protein HLA–DR1 complexed with an influenza virus peptide," *Nature* 368:215–221 (1994).

Szabo SJ et al., "Regulation of the interleukin (IL)–12R beta 2 subunit expression in developing T helper 1 (Th1) and Th2 cells," *J Exp Med* 185:817–824 (1997).

Taneja V, et al., "HLA transgenic mice as humanized mouse models of disease and immunity," *J Clin Invest* 101:921–926 (1998).

Todd JA et al., "A moleclar basis for MHC class II—associated autoimmunity," *Science* 240:1003–1009 (1988).

Vallejo AN, et al., "Aging–related deficiency of CD28 expression in CD4+ T cells is associated with the loss of gene–specific nuclear factor binding activity," *J Biol Chem* 273(14):8119–8129 (1998).

Van Roon JA et al., "Prevention and reversal of cartilage degradation in rheumatoid arthritis by interleukin–10 and interleukin–4," *Arthritis Rheum* 39:829–835 (1996).

Waase I, et al., "Oligoclonal T cell proliferation in patients with rheumatoid arthritis and their unaffected siblings," *Arthritis Rheum* 39:904–913 (1996).

Wagner UG, et al., "The role of CD8+ CD40L+ T cells in the formation of germinal centers in rheumatoid synovitis," *J Immunol* 161:6390–6397 (1998).

Wakeland E, et al., "Speed congenics: a classic technique in the fast lane (relatively speaking)," *Immunol Today*, (1997), 18:472–477.

Walmsley M et al., "Interleukin–10 inhibition of the progression of established collagen–induced arthritis," *Arthritis Rheum* 39:495–503 (1996).

Walser–Kuntz DR, et al., "Mechanisms underlying the formation of the T cell receptor repertoire in rheumatoid arthritis," *Immunity* 2:597–605 (1995).

Weyand CM, et al., "Correlation between disease phenotype and genetic heterogeneity in rheumatoid arthritis," *J Clin Invest* 95:2120–2126 (1995).

Weyand CM et al., "Disease patterns and tissue cytokine profiles in giant cell arteritis," *Arthritis Rheum* 40:19–26 (1997).

Weyand CM, et al., "Functional properties of CD4+ CD28– T cells in the aging immune system," *Mech Age Develop* 102(2–3):131–147 (1998).

Weyand CM, et al., "HLA–DRB1 alleles in polymyalgia rheumatica, giant cell arteritis, and rheumatoid arthritis," *Arthritis Rheum* 37:514–520 (1994).

Weyand CM, et al., "Homozygosity for the HLA–DRB1 allele selects for extraarticular manifestations in rheumatoid arthritis," *J Clin Invest* 89:2033–2039 (1992).

Weyand CM, et al., "Inherited and noninherited risk factors in rheumatoid arthritis," *Curr Opin Rheumatol* 7:206–213 (1995).

Weyand CM et al., "Pathogenesis of rheumatoid arthritis," *Med Clin North Am* 81:29–55 (1997).

Weyand CM, et al., "The influence of HLA–DRB1 genes on disease severity in rheumatoid arthritis," *Ann Intern Med* 117:801–806 (1992).

Weyand CM et al., "Tissue cytokine patterns in patients with polymyalgia rheumatica and giant cell arteritis," *Ann Intern Med* 121:484–491 (1994).

Wicker LS, et al., "Genetic control of autoimmune diabetes in the NOD mouse," *Annu Rev Immunol*, (1995), 13:179–200.

Willkens RF, et al, "Association of HLA–Dw16 with rheumatoid arthritis in Yakima Indians. Further evidence for the "shared epitope" hypothesis," *Arthritis Rheum* 34:43–47 (1991).

Winchester R., "The molecular basis of susceptibility to rheumatoid arthritis," *Adv Immunol* 56:389–466 (1994).

Yamamura M et al., "Defining protective responses to pathogens: cytokine profiles in leprosy lesions," *Science* 254:277–279 (1991).

* cited by examiner

METHODS AND MATERIALS FOR EVALUATING RHEUMATOID ARTHRITIS

RELATED APPLICATIONS

This application claims priority from U.S. Provisional Application Serial No. 60/098,718, filed Sep. 1, 1998.

STATEMENT AS TO FEDERALLY SPONSORED RESEARCH

Support in the development of the invention described herein was provided by the National Institutes of Health, Grant Numbers AR42527 and AR41974, which may have certain rights in the invention.

BACKGROUND

1. Technical Field

The invention relates to methods and materials for evaluating rheumatoid arthritis as well as for determining an individual's predisposition to have severe rheumatoid arthritis disease.

2. Background Information

Rheumatoid arthritis (RA) affects individuals in the prime of their life and is feared because of its potential to cause chronic pain and irreversible damage of tendons, ligaments, joints, and bones. The symmetrical involvement of small peripheral joints has an enormous impact on hand and foot functions and poses therapeutic challenges that cannot be easily overcome by joint replacement. Also, systemic manifestations of RA are not rare and can range from relatively minor problems, such as rheumatoid nodules, to life-threatening organ disease.

In addition, RA is a systemic inflammatory disease that primarily manifests itself as synovial inflammation of diarthrodial joints. The typical histopathological changes include dense infiltration of the synovial membrane by mononuclear cells, neoangiogenesis, and hypertrophy and hyperplasia of the synovial lining (Harris E D (ed); Rheumatoid Arthritis, Philadelphia, WB Saunders Co., pp.3–212 (1997); and Hale L P, Haynes B F: Pathology of rheumatoid arthritis and associated disorders. Arthritis and Allied Conditions. A textbook of Rheumatology. Edited by Koopman W J. Baltimore, Williams & Wilkins, pp.993–1016 (1997)). The etiopathogenesis of the syndrome is not understood. Several lines of evidence support a central role of T lymphocytes in the disease-specific pathogenic events (Todd, et al. *Science*, 240:1003–1009 (1988); Panayi, et al., *Arthritis Rheum*, 35:729–735 (1992); and Goronzy J J, Weyand C M: *Rheum Dis Clin North Am*, 21:655–674 (1995)). An alternative hypothesis, namely, that macrophages are the pivotal cell type in rheumatoid synovitis, has also been proposed (Firestein G S, Zvaifler N J: *Arthritis Rheum* 33:768–773 (1990); and Burmester, et al., *Arthritis Rheum*, 40:5–18 (1997)). Whether only T cells or only macrophages or both are the causative elements in RA remains a matter of controversy (Feldmann, et al., *Cell*, 85:307–310 (1996); and Fox, *Arthritis Rheum* 40:598–609 (1997)).

RA is primarily a clinical diagnosis. Symmetrical joint involvement, dominant manifestations in peripheral joints, rheumatoid factor production, and the formation of rheumatoid nodules are considered when the diagnosis is made (Arnett, et al., *Arthritis Rheum*. 31:315–324 (1988)). The histological appearance of the synovium varies quite extensively and the pathological findings are usually not helpful in distinguishing RA from other inflammatory arthropathies (Hale L P, Haynes B F: Pathology of rheumatoid arthritis and associated disorders. Arthritis and Allied Conditions. A textbook of Rheumatology. Edited by Koopman W J. Baltimore, Williams & Wilkins, pp.993–1016 (1997)). In addition, no information is available on the mechanisms underlying the topographical arrangement of the inflammatory infiltrate in the rheumatoid synovium.

Therapeutic management of RA has steadily improved over the last decades, mostly due to the recognition that destruction caused by chronic inflammation is irreversible and that only early and aggressive intervention can enhance therapeutic benefit. Consequently, RA patients are now being treated early in the disease course and disease modifying agents are widely used. Despite these successes, major challenges remain. Presently, no curative intervention is available, side effects of therapies are significant, and the disease may still progress while the patient is being treated.

SUMMARY

The invention involves methods and materials for evaluating rheumatoid arthritis in a patient. Specifically, the invention provides methods and materials for classifying a rheumatoid arthritis condition as diffuse, follicular, or granulomatous. In addition, the invention provides methods and materials for determining if an individual suffering from a rheumatoid arthritis condition will develop severe disease. Useful indicators for severe disease include, without limitation, subcutaneous nodule formation (nodularity) and extra-articular involvement.

The invention is based on the discovery that the level of particular cytokines within tissue or the histological appearance of tissue or both can be used to classify a rheumatoid arthritis condition as diffuse, follicular, or granulomatous. This classification is important since granulomatous patients are more susceptible to severe rheumatoid arthritis disease. Severe rheumatoid arthritis disease can involve, without limitation, major organ involvement, which can be life threatening, and major joint destruction, which can be crippling. Thus, proper classification of a granulomatous rheumatoid arthritis condition can help provide clinicians and patients with information that can be used to determine adequate treatments.

Specifically, the invention involves analyzing a synovial tissue biopsy for particular cytokines such as IL-4, IL-10, and IFN-$\gamma$, or for particular histological characteristics, or both. For example, a patient can be classified as having a diffuse condition when tissue from that patient contains low levels of IL-4, IL-10, and IFN-$\gamma$, or as having a follicular condition when tissue from that patient contains high levels of IL-10 and IFN-$\gamma$ and low levels of IL-4. A particular level of a particular cytokine can be determined to be high or low based on the levels measured from various populations. Such populations can include, without limitation, populations of patents with a diffuse condition, follicular condition, or granulomatous condition, patients with subcutaneous nodule formation, patients with extra-articular involvement, patients with major joint destruction, and healthy individuals.

The invention also is based on the discovery that patients presenting similar rheumatoid arthritis symptoms can have different levels of particular cytokines within their tissue or different histological appearance of their tissue. Thus, determining the tissue cytokine profile or the histological characteristics of a synovial tissue sample from a patient can be used to determine the proper treatment protocol. For example, two patients having similar rheumatoid arthritis symptoms may have different levels of IL-10 within their tissue. The patient with low levels may benefit from a treatment of IL-I 0 while the patient with high levels of IL-10 may benefit from treatment with IL-10 inhibitors such as anti-IL-10 antibodies. Thus, determining the tissue cytokine profile or the histological characteristics of a tissue sample from a patient can help provide clinicians and patients with information that can be used to determine adequate treatments.

In addition, the invention is based on the discovery that the predisposition to develop severe disease can be determined in patients classified as having diffuse or follicular disease by analyzing the patient's HLA-DRB1 alleles or frequency of $CD4^+/CD28^{null}$ cells or both. Determining a patient's predisposition to develop severe disease is important since it allows clinicians and patients to plan and treat accordingly. Again, severe rheumatoid arthritis disease can involve, without limitation, extra-articular involvement and major joint destruction. Moreover, analyzing a patient's HLA-DRB1 alleles and/or frequency of $CD4^+/CD28^{null}$ cells can be used to determine whether a patient classified as having diffuse or follicular disease with a propensity for severe disease will have major organ damage, major joint destruction, or both.

Specifically, the invention involves determining whether a patient having a diffuse or follicular condition has zero, one, or two HLA-DRB1 alleles that are associated with RA and/or whether that patient has an elevated frequency of $CD4^+/CD28^{null}$ cells. For example, HLA-DRB1 alleles that are associated with RA can be any allele having a polymorphism associated with rheumatoid arthritis including HLA-DRB1 alleles that encode polypeptides having an uncharged amino acid at position 74, no negatively charged amino acid at position 70, and a positively charged amino acid at position 71. Patients having RA-associated polymorphisms for one or both HLA-DRB1 alleles or having an elevated frequency of $CD4^+/CD28^{null}$ cells can be classified as having the potential to form severe disease.

In general, the invention features a method for diagnosing a rheumatoid arthritis condition in a patient. The method includes determining the level of a cytokine (e.g., IL-4, IL-10, and IFN-γ) within a sample from the patient, comparing the level of the cytokine to a reference level to obtain information about the rheumatoid arthritis condition, and classifying the rheumatoid arthritis condition as a diffuse, follicular, or granulomatous condition based on the information. The sample can be a tissue biopsy (e.g., a synovial tissue biopsy). The reference level can be the median level of the cytokine found in tissue samples derived from a population. The population can include a population of patients having a diffuse rheumatoid arthritis condition, a population of patients having a follicular rheumatoid arthritis condition, a population of patients having a granulomatous rheumatoid arthritis condition, a population of healthy individuals, a population of patients having subcutaneous nodules, a population of patients having extra-articular involvement, or a population of patients having major joint destruction.

In another embodiment, the invention features a method for determining the predisposition of a rheumatoid arthritis patient to develop severe disease. The method includes determining the level of a cytokine (e.g., IL-4, IL-10, and IFN-γ) within a sample from the patient, determining the frequency of $CD4^+/CD28^{null}$ cells in the patient, comparing the level of the cytokine to a reference level and the frequency of $CD4^+/CD28^{null}$ cells to a reference frequency to obtain information about the predisposition, and determining if the patient is predisposed to develop severe disease based on the information. The sample can be a tissue biopsy (e.g., a synovial tissue biopsy). The reference level can be the median level of a the cytokine found in tissue samples derived from a population. The population can include a population of patients having a diffuse rheumatoid arthritis condition, a population of patients having a follicular rheumatoid arthritis condition, a population of patients having a granulomatous rheumatoid arthritis condition, a population of healthy individuals, a population of patients having subcutaneous nodules, a population of patients having extra-articular involvement, or a population of patients having major joint destruction. The frequency of $CD4^+/CD28^{null}$ cells can be the percent of $CD4^+$ cells that are CD28 negative. In addition, the reference frequency can be derived from the $CD4^+/CD28^{null}$ cell frequency from a population.

Another embodiment of the invention features a method for determining the predisposition of a rheumatoid arthritis patient to develop severe disease. The method includes determining the level of a cytokine (e.g., IL-4, IL-10, and IFN-γ) within a sample from the patient, comparing the level of the cytokine to a reference level to obtain information about the rheumatoid arthritis condition, determining the presence of a polymorphism in an HLA-DRB1 allele in the patient, and determining if the patient is predisposed to develop severe disease based on the information and the presence of the polymorphism. The sample can be a tissue biopsy (e.g., a synovial tissue biopsy). The reference level can be the median level of the cytokine found in tissue samples derived from a population. The population can include a population of patients having a diffuse rheumatoid arthritis condition, a population of patients having a follicular rheumatoid arthritis condition, a population of patients having a granulomatous rheumatoid arthritis condition, a population of healthy individuals, a population of patients having subcutaneous nodules, a population of patients having extra-articular involvement, or a population of patients having major joint destruction. The polymorphism can include an HLA-DRB1 allele that encodes a polypeptide having an uncharged amino acid at position 74, or an HLA-DRB1 allele that encodes a polypeptide free from negatively charged amino acids at positions 70 and 71.

Another embodiment of the invention features a method for determining the predisposition of a rheumatoid arthritis patient to develop severe disease. The method includes determining the level of a cytokine within a sample from the patient, determining the frequency of $CD4^+/CD28^{null}$ cells in the patient, comparing the level of the cytokine to a reference level and the frequency of $CD4^+/CD28^{null}$ cells to a reference frequency to obtain information about the rheumatoid arthritis condition, determining the presence of a polymorphism in an HLA-DRB1 allele in the patient, and determining if the patient is predisposed to develop severe disease based on the information and the presence of the polymorphism.

In another aspect, the invention features a kit for providing diagnostic information about a rheumatoid arthritis condition in a patient. The kit contains a binding pair member and a reference chart. The binding pair member has specific binding affinity for a cytokine such that the level of the cytokine within a sample from the patient is determinable, and the reference chart contains information about cytokine levels such that an indication of the diffuse, follicular, or granulomatous nature of the rheumatoid arthritis condition is determinable based on the level of the cytokine within the sample.

In another embodiment, the invention features a kit for providing diagnostic information about a rheumatoid arthritis condition in a patient. The kit contains a binding pair member and a reference chart. The binding pair member has specific binding affinity for a nucleic acid sequence encoding a cytokine such that the level of the cytokine within a sample from the patient is determinable, and the reference chart contains information about cytokine levels such that an indication of the diffuse, follicular, or granulomatous nature of the rheumatoid arthritis condition is determinable based on the level of the cytokine within the sample.

In another embodiment, the invention features a kit for determining the predisposition of a rheumatoid arthritis patient to develop severe disease. The kit contains a first binding pair member, a second binding pair member, and a reference chart. The first binding pair member has specific binding affinity for a cytokine or nucleic acid encoding the cytokine such that the level of the cytokine within a sample from the patient is determinable. The second binding pair member has specific binding affinity for a $CD4^+/CD28^{null}$ cell marker such that the frequency of $CD4^+/CD28^{null}$ cells in the patient is determinable. The reference chart contains information about cytokine levels and $CD4^+/CD28^{null}$ cell frequencies such that an indication of the predisposition is determinable based on the level of the cytokine within the sample and the frequency of $CD4^+/CD28^{null}$ cells in the patient.

In another embodiment, the invention features a kit for determining the predisposition of a rheumatoid arthritis patient to develop severe disease. The kit contains a binding pair member, an oligonucleotide primer, and a reference chart. The binding pair member has specific binding affinity for a cytokine or nucleic acid encoding the cytokine such that the level of the cytokine within a sample from the patient is determinable. The oligonucleotide primer has specific binding affinity for at least a portion of the locus containing an HLA-DRB1 allele such that a polymorphism of HLA-DRB1 allele in the patient is determinable. The reference chart contains information about cytokine levels such that an indication of the predisposition is determinable based on the level of the cytokine within the sample and the polymorphism of the patient. The kit can contain a plurality of the oligonucleotide primers.

In another embodiment, the invention features a kit for determining the predisposition of a rheumatoid arthritis patient to develop severe disease. The kit contains a first binding pair member, a second binding pair member, an oligonucleotide primer, and a reference chart. The first binding pair member has specific binding affinity for a cytokine or nucleic acid encoding the cytokine such that the level of the cytokine within a sample from the patient is determinable. The second binding pair member has specific binding affinity for a $CD4^+/CD28^{null}$ cell marker such that the frequency of $CD4^+/CD28^{null}$ cells in the patient is determinable. The oligonucleotide primer has specific binding affinity for at least a portion of the locus containing an HLA-DRB1 allele such that the a polymorphism of the HLA-DRB1 allele in the patient is determinable. The reference chart contains information about cytokine levels and $CD4^+/CD28^{null}$ cell frequencies such that an indication of the predisposition is determinable based on the level of the cytokine within the sample, the frequency of $CD4^+/CD28^{null}$ cells in the patient, and the polymorphism of the HLA-DRB1 allele.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1:
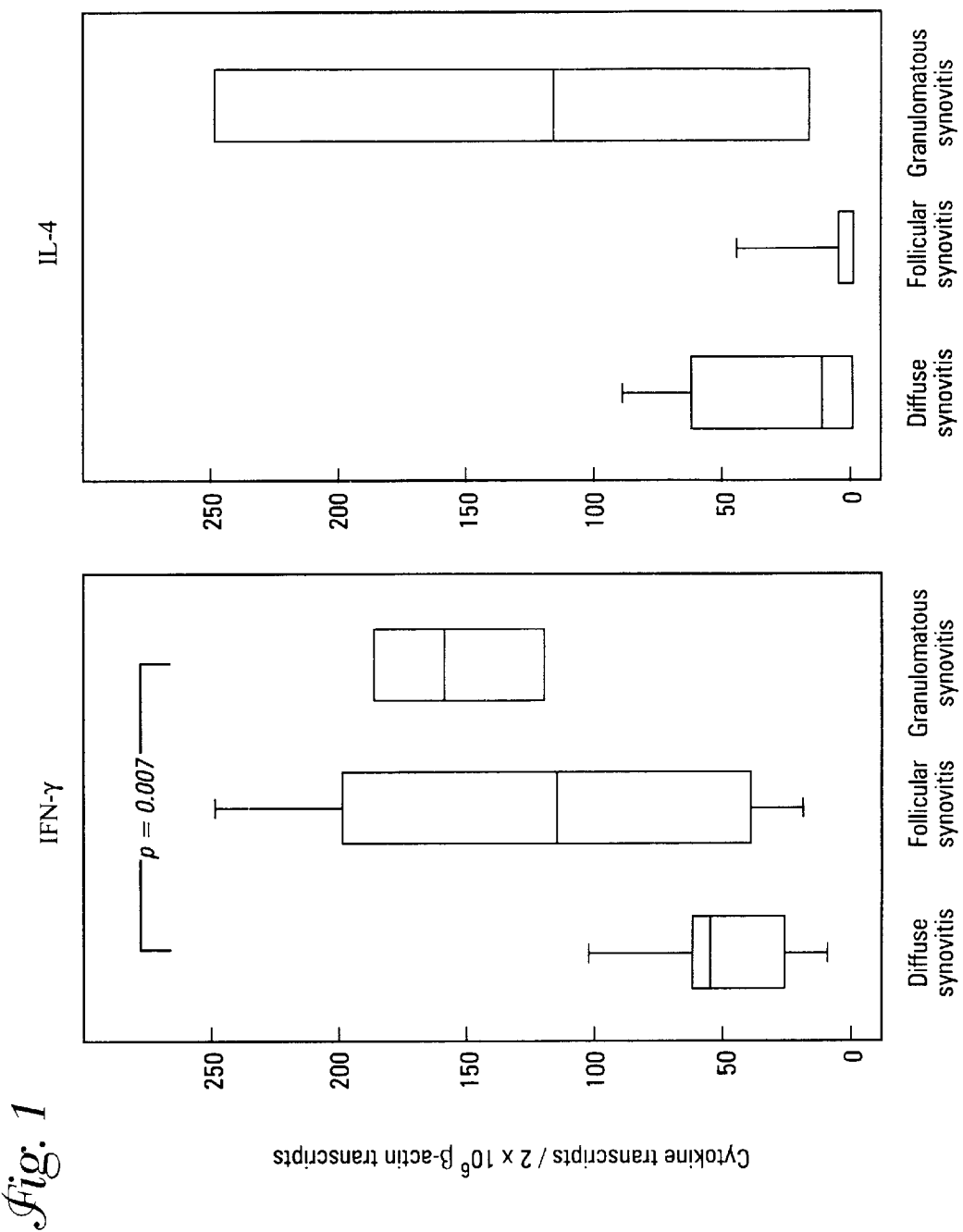
FIG. 1 contains two bar graphs plotting the number of cytokine transcripts (IFN-γ and IL-4) per β-actin transcripts for diffuse, follicular, and granulomatous synovial tissues.

The invention provides methods and materials for evaluating rheumatoid arthritis in a patient. Specifically, the invention provides methods and materials for classifying a rheumatoid arthritis condition as diffuse, follicular, or granulomatous. In addition, the invention provides methods and materials for determining a patient's predisposition to develop severe rheumatoid arthritis disease.

RA can be classified as diffuse, follicular, or granulomatous based on either the profile of cytokines produced within a synovial tissue sample or the histological characteristics of a synovial tissue sample. Any method can be used to quantify specific cytokine expression within synovial tissue including methods that measure cytokine mRNA or cytokine polypeptide. For example, PCR, competitive PCR, PCR-ELISA, and in situ hybridization techniques can be used to measure cytokine mRNA. In addition, ELISA, immunohistochemistry and other immuno assays can be used to measure cytokine polypeptide. Such cytokines can be, without limitation, IFN-γ, IL-2, IL-4, IL-5, IL-6, IL-10, and IL-12. The histological characteristics of a synovial tissue sample can be determined using common staining techniques that reveal the presence of macrophages and lymphocytes such as H &E staining and immunocytochemistry.

If the cytokine profiles or histological characteristics indicate that a patient has granulomatous disease than that patient also can be classified as being predisposed to develop a severe rheumatoid arthritis condition including major organ involvement and major joint destruction since granulomatous disease was discovered herein to correlate with severe disease. If the cytokine profiles or histological characteristics indicate that a patient has diffuse or follicular disease than further analysis can be performed to determine that patient's predisposition to develop severe disease. This further analysis can involve analyzing the HLA-DRB1 locus for alleles having polymorphisms associated with RA and/or determining the CD4$^+$/CD28$^{null}$ T cell frequency.

Determining whether a patient has zero, one, or two HLA-DRB1 alleles that contain a polymorphism associated with RA can be accomplished using commonly known methods such as PCR, PCR-ELISA, and sequencing. For example, any method provided by the International Histocompatibility Workshop can be used as well as any commercially available methods of materials obtained from, for example, One Lambda (Los Angles, Calif.) or Biotest Diagnostics (Denville, N.J.). Such HLA-DRB1 alleles can include, without limitation, HLA-DRB1 alleles that encode a polypeptide having an uncharged amino acid at position 74, no negatively charged amino acid at position 70, and a positively charged amino acid at position 71.

Any method can be used to determine the frequency of CD4$^+$/CD28$^{null}$ T cells within a patient. For example, a binding pair member having specificity for a marker found on CD4$^+$/CD28$^{null}$ cells can be used to determine the frequency of those cells. Such a method can involve using the combination of two antibodies, one having specificity for CD4 and the other having specificity for CD28. For example, FACS can be used with CD4 and CD28 specific antibodies to determine the percent of CD4$^+$ cells that are CD28 negative. Further, CD3 antibodies can be used to distinguish CD4$^+$ T cells from CD4$^+$ macrophages.

Once a frequency of CD4$^+$/CD28$^{null}$ cells in a patient is determined, that frequency can be compared to a reference frequency to obtain information about the patient's RA condition. Typically, a reference frequency is derived from the CD4$^+$/CD28$^{null}$ cell frequencies determined for a population of individuals. For example, a reference frequency can be a median percent of CD4$^+$ cells that are CD28 negative as derived from a population. The population can be a population of healthy individuals or patients having subcutaneous nodularity, extra-articular involvement, major joint destruction, diffuse disease, follicular disease, and/or granulomatous disease. The information obtained by this comparison can allow the patient's RA condition to be classified as either severe or not severe. For example, if the frequency of CD4$^+$/CD28$^{null}$ cells from a patient corresponds to the reference frequency of CD4$^+$/CD28$^{null}$ cells derived from a population of healthy individuals and that patient has diffuse disease and no RA-associated HLA-DRB1 alleles, then that patient would not be classified as being predisposed to develop severe RA disease. Likewise, if the frequency of CD4$^+$/CD28$^{null}$ cells from a patient corresponds to the reference frequency of CD4$^+$/CD28$^{null}$ cells derived from a population of patients having subcutaneous nodularity and that patient has diffuse and no RA-associated DRB1 alleles, then that patient can be classified as being predisposed to develop severe RA disease. Typically, a patient having diffuse RA disease with greater than about 2.0% of their CD4$^+$ cells being CD28 negative has a predisposition to develop severe RA disease.

A reference chart is any chart that contains information about cytokine levels, HLA-DRB1 alleles, or CD4$^+$/CD28$^{null}$ T cell frequencies. For example, a reference chart can contain information about the average frequency of CD4$^+$/CD28$^{null}$ cells found in a particular population of individuals or patients. It will be appreciated that a reference chart can be presented or contained on any type of medium (e.g., paper or electronic formats). It is to be understood that an electronic format can be obtained via a software program or an accessible database site (e.g., an Internet site). For the purpose of this invention, kits containing a reference chart include kits having directions (e.g., access codes or Internet address information) for accessing reference charts in an electronic format.

A binding pair member is any molecule that specifically binds another molecule including, without limitation, antibodies, antibody fragments that have binding specificity, ligands, nucleic acid, receptors, lectins, chelating agents, ions, and the like.

The invention will be further described in the following examples, which do not limit the scope of the invention described in the claims.

EXAMPLES

Example 1

Three Distinct Histopathological Patterns in Rheumatoid Synovitis

The pattern of cytokines produced in the rheumatoid synovium was found to be predictive of the morphological appearance of the disease. Specifically, rheumatoid synovitis was found to be a heterogeneous entity with three distinct histologically defined phenotypes. The phenotypic heterogeneity correlated to a specific combination of T-cell- and macrophage-derived cytokines, raising the possibility that several pathomechanisms may cause an RA-like syndrome.

1. Study Population

Fresh synovial tissue was obtained from 21 consecutive patients with active RA who fulfilled the American College of Rheumatology 1987 revised criteria for RA (Arnett, et al., *Arthritis Rheum*, pp.31:315–324 (1988)) and who underwent joint surgery.

2. Histopathological Evaluations

Hematoxylin and eosin sections of the tissue samples were analyzed for the organizational structure of the inflammatory infiltrate with particular attention to the topographical arrangement of T cells, B cells, and macrophages as well as the degree of angiogenesis and the relationship of the mononuclear infiltrate to the subsynovial lining. All tissue samples were reviewed by a pathologist who was unaware of any clinical, seriological, or immunohistological findings. To control for patchiness of the inflammation and intra-specimen variation, multiple independent specimens were included from ten patients with the pathologist blinded to the identity of the specimens. There was concordance for the identification of follicles and granulomatous lesions for all of the independently graded specimens.

3. Immunohistochemistry

Frozen tissue samples embedded in OCT (Miles, Elkhart, Ind.) were cut into 5-$\mu$m sections, mounted on the gel-coated slides (Superfrost/Plus, Fisher Scientific, Pittsburgh, Pa.), and dried in a 37° C. desiccator. Slides were stored at −70° C. Before staining, slides were fixed in acetone for ten minutes, air dried, and fixed in a 1% paraformaldehyde/EDTA, pH 7.2, for three minutes. Endogenous peroxidase was blocked with 0.3% $H_2O_2$ in 0.1% sodium azide. Non-specific binding was blocked with 5% rabbit serum (Life Technologies, Grand Island, N.Y.) for 15 minutes. Sections were stained with monoclonal mouse anti-interferon (IFN)-$\gamma$ Ab, 1:100 (Genzyme Diagnostics, Cambridge, Mass.) for 60 minutes or monoclonal mouse anti-CD20 Ab, 1:40 (Dako, Carpinteria, Calif.) for 30 minutes at room temperature. After incubation with biotinylated rabbit anti-mouse antibody, 1:300 (Dako), the slides were developed with streptavidin-peroxidase, 1:250 (Dako) and 3,3'-diaminobenzidine tetrahydrochloride (Sigma Chemical Co., St. Louis, Mo.).

Slides stained with anti-IFN-γ were washed in 0.5%Triton X-100 in PBS for ten minutes. Nonspecific binding was blocked for 15 minutes with 5% normal goat serum (Life Technologies). Sections were stained with a monoclonal mouse anti-CD45RO Ab, 1:60 (Dako), for 30 minutes at room temperature. After incubation with a biotinylated rabbit anti-mouse antibody, 1:300 (Dako), the slides were developed with a Vectastain ABC-AP kit and alkaline phosphatase substrate kit 1 (Vector Laboratories, Burlingame, Calif.). Negative controls without primary Ab were processed in parallel. Sections were counterstained with hematoxylin and permanently mounted in Cytoseal (Stephens Scientific, Riverdale, N.J.).

4. Cytokine Measurement

Total RNA was extracted from synovial tissue by using a commercially available kit (Trizol, Life Technologies). cDNA from synovial tissue specimens was adjusted to contain equal numbers of β-actin transcripts. Adjusted cDNA was amplified under nonsaturating conditions with cytokine-specific primers (Table 1) by polymerase chain reaction (PCR) in parallel with a standard with a known number of cytokine sequences as described (Weyand, et al., *Arthritis Rheum*, pp.40:19–26 (1997)). Primers were chosen to amplify cDNA specifically and not genomic DNA. To achieve this goal, several primers had been designed to span an intron (Brack, et al., *J Clin Invest*, pp.99:2842–2850 (1997)). Amplified products were labeled with digoxygenin-11-dUTP (Boehringer Mannheim, Indianapolis, Ind.) and then semiquantified in a liquid hybridization assay with biotinylated internal probes (Table 1) using a commercially available PCR ELISA kit (Boehringer Mannheim). In this assay, the labeled PCR products were hybridized with 200 ng/mL probe at 42° C. for β-actin, interleukin (IL)-4, IFN-γ, transforming growth factor (TGF)-β1, and tumor necrosis factor (TNF)-α and at 55° C. for IL-1β and IL-10 for two hours. Hybrids were immobilized on streptavidin-coated microtiter plates and, after washing, were detected with a peroxidase-labeled anti-digoxigenin antibody. Plates were developed by a color reaction using ABTS (2,2'-azino-di[3-ethylbenzthiazoline sulfonate] diammonium salt) substrate and quantitated using a kinetic microplate reader (Molecular Devices, Sunnyvale, Calif.). The number of cytokine-specific sequences was determined by interpolation with a standard curve and was expressed as the number of cytokine sequences per $2 \times 10^6$ β-actin sequences.

TABLE 1

Nucleotide Sequences of PCR Primers and Biotinylated Probes

| | | Oligonucleotide sequence |
|---|---|---|
| β-Actin | 5' Primer | ATG GCC ACG GCT GCT TCC AGC |
| | 3' Primer | CAT GGT GGT GCC GCC AGA CAG |
| | Probe | TAC AGG TCT TTG CGG ATG TC |
| IL-1β | 5' Primer | GAC ACA TGG GAT AAC GAG GC |
| | 3' Primer | GGG ATC TAC ACT CTC CAG CTG |
| | Probe | AGC TTT TTT GCT GTG AGT CCC GGA G |
| IL-4 | 5' Primer | CTT CCC CCT CTG TTC TTC CT |
| | 3' Primer | TTC CTG TCG AGC CGT TTC AG |
| | Probe | AGA GCA GAA GAC TCT GTG CAC CGA G |

TABLE 1-continued

Nucleotide Sequences of PCR Primers and Biotinylated Probes

| | | Oligonucleotide sequence |
|---|---|---|
| IL-10 | 5' Primer | CAG TTT TAC CTG GAG GAG |
| | 3' Primer | CAA TAA GGT TTC TCA AGG GGC TGG GTC |
| | Probe | CTA CGG CGC TGT CAT CGA TTT CTT |
| IFN-γ | 5' Primer | ACC TTA AGA AAT ATT TTA ATG C |
| | 3' Primer | ACC GAA TAA TTA GTC AGC TT |
| | Probe | ATT TGG CTC TGC ATT ATT TTT CTG T |
| TGF-β1 | 5' Primer | AAG TGG ACA TCA ACG GGT TCA CTA |
| | 3' Primer | GCT GCA CTT GCA GGA GCG CAC |
| | Probe | ATC TGC AAA GCT CCC GGC AC |
| TNF-α | 5' Primer | TAG CCC ATG TTG TAG CAA ACC C |
| | 3' Primer | TCG GCA AAG TCG AGA TAG TC |
| | Probe | AAT GGC GTG GAG CTG AGA GAT AAC |

5. Statistical Analysis

The clinical presentations of the histopathology defined patient subsets were compared by using a Fisher's exact test. In situ cytokine production was compared using a nonparametric Kruskal-Wallis test.

6. Results

Microscopic evaluation of rheumatoid synovium revealed fibrin exudation and hyperplasia of synovial lining cells, often assuming a villous configuration, stromal fibrosis, capillary angiogenesis, and diffuse stromal inflammation. Tissue-infiltrating cells included T cells, macrophages, and B cells. Giant cells were variably present. To identify pathological patterns of the synovial inflammation, a series of 21 tissues from patients undergoing joint surgery was analyzed. To exclude features due to long standing and burned out diseases, only patients with clinically active synovitis were enrolled.

Upon analysis by conventional histology, three patterns emerged. Ten tissue samples were categorized as diffuse synovitis (Table 2). These tissues were characterized by a diffuse infiltrate of lymphocytes and macrophages without any additional microanatomical arrangements. The infiltrate tended to be sparse and was accompanied by moderate edema as well as delicate and diffuse fibrosis. A second pattern manifested as demarcated lymphocytic aggregates with sparing of the intervening stroma. In some patients, indistinct germinal center formation with central clearing of the aggregates was apparent. Immunohistochemical analysis showed that follicular structures displayed a central accumulation of B cells surrounded by T cells. Such pseudofollicular organizations were detected in seven tissues and were classified as follicular synovitis. Four patients displayed necrobiotic granulomas. In this pattern, a fibrinoid necrotic center was lined by a collar of epithelioid histiocytes with or without giant cells. External to this palisade, or garland, of histiocytes was a zone of granulation tissue with angiogenesis and a mixed inflammatory infiltrate composed of lymphocytes, histiocytes (macrophages), and plasma cells. No specimens displayed both follicular synovitis and granulomatous necrobiosis.

Each specimen was evaluated further with respect to fibrinous exudates, capillary neovacularization, and linear subsynovial inflammatory arrays. These features were variable and were not correlated with each other or any of the three main inflammatory patterns.

TABLE 2

Histomorphological Characteristics of Rheumatoid Synovium

| Patient | Diffuse infiltrate | Follicle formation | Granuloma formation |
|---|---|---|---|
| RA 1 | + | − | − |
| RA 2 | + | − | − |
| RA 3 | + | − | − |
| RA 4 | + | − | − |
| RA 12 | + | − | − |
| RA 13 | + | − | − |
| RA 14 | + | − | − |
| RA 15 | + | − | − |
| RA 18 | + | − | − |
| RA 21 | + | − | − |
| RA 7 | + | + | − |
| RA 8 | + | + | − |
| RA 10 | + | + | − |
| RA 16 | + | + | − |
| RA 17 | + | + | − |
| RA 19 | + | + | − |
| RA 20 | + | + | − |
| RA 5 | + | − | + |
| RA 6 | + | − | + |
| RA 9 | + | − | + |
| RA 11 | + | − | + |

Example 2

T-cell Derived Cytokines in Distinct Types of Rheumatoid Synovitis

A semiquantitative PCR/liquid hybridization assay was used to detect low concentrations of cytokines in tissue extracts. To directly address the question of whether a correlation exists between the tissue organization of inflammatory cells and cytokine production, the three histomorphologically defined types of synovitis were compared for in situ transcription of the IFN-γ and IL-4 genes. To correct for variations in the amount of tissue used for RNA extraction, all cDNAs were adjusted to a concentration equivalent to $2 \times 10^6$ copies of the β-actin gene product (FIG. 1). IFN-γ mRNA production was a characteristic finding for granulomatous synovitis. Tissues with follicular synovitis contained variable concentrations of IFN-γ mRNA copies (median of 114 copies) whereas the lowest levels were found in extracts derived from material with diffuse synovitis (median of 55 copies). As demonstrated by two-color immunohistochemistry, the major IFN-γ producing cells in all three forms of synovitis were T cells. The high rate of IFN-γ transcription distinguished patients with granuloma formation from the diffuse subtype (P=0.007).

A different pattern of tissue distribution was seen for IL-4 mRNA. IFN-γ and IL-4 are both derived from T cells, but they are usually secreted by distinct subsets of T helper cells. T cells with a commitment to the $T_H1$ pathway release IFN-γ and IL-2. Conversely, IL-4 is the typical product of a $T_H2$ cell. IFN-γ and IL-4 can be considered as antagonistic effectors with IFN-γ driving inflammatory responses and IL-4 acting as an anti-inflammatory mediator. The highest concentration of IL-4 mRNA was determined in samples with granulomatous synovitis (median of 116 copies). IL-4 transcripts were essentially absent in biopsies from patients with follicular synovitis and were detectable only at low levels in diffuse synovitis.

Taken together, the studies on T-cell derived cytokines indicated that diffuse synovitis correlated with low concentrations of IFN-γ and IL-4 mRNA. This pattern might indicate a low degree of activation of predominantly non-committed $T_H0$ cells. Follicular synovitis followed the paradigm for germinal centers in that IFN-γ was the dominant T cell product and IL-4 was virtually absent. This type of RA would be best described as a $T_H1$ mediated response. The constellation of high levels of IFN-γ combined with high transcription of IL-4 mRNA found in granulomatous synovitis did not fit the current paradigm. The presence of IL-4 mRNA was surprising and raised the question of how these two antagonistic cytokines can co-exist in the lesions.

Example 3

Figure 2:
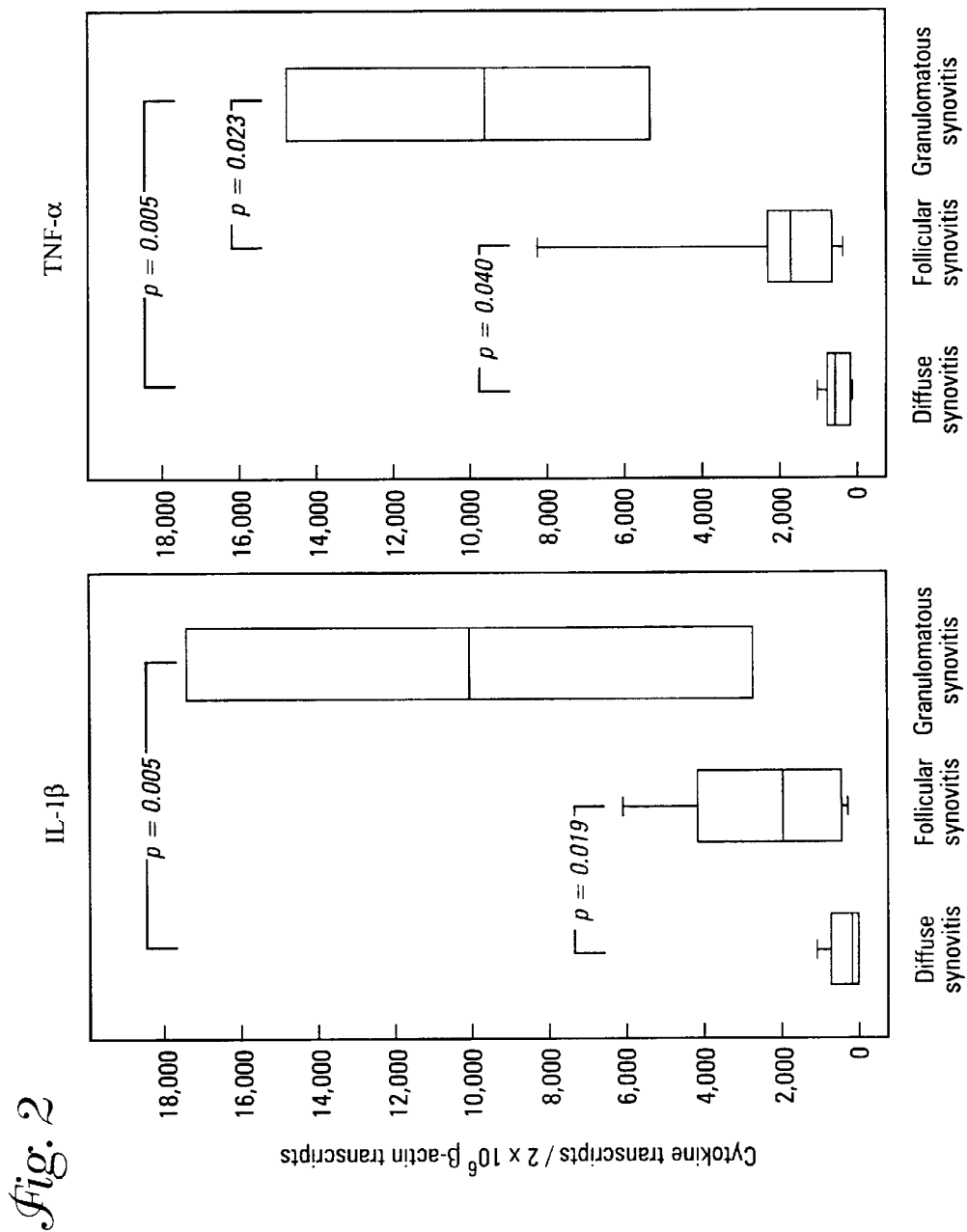
FIG. 2 contains two bar graphs plotting the number of cytokine transcripts (IL-1β and TNF-α) per β-actin transcripts for diffuse, follicular, and granulomatous synovial tissues.

Differences in Macrophage Activation Distinguish the Three Variants of Rheumatoid Synovitis To address the question of whether the different organizational forms of rheumatoid synovitis are associated with differences in the activation of synovial macrophages, the number of IL-1β and TNF-α transcripts were determined in the tissue extracts. IL-1β and TNF-α specific sequences were detected in all samples. As shown in FIG. 2, concentrations of in situ transcribed IL-1β varied extensively, ranging from 103 to 17,400 copies per $2 \times 10^6$ β-actin sequences. Low copy numbers were frequently found in specimens with diffuse synovitis (median of 270 copies), and intermediate levels of IL-1β transcription were typical for follicular synovitis (median of 2038 copies). This difference was statistically significant (P=0.019). Tissue sections with granuloma formation had the highest rate of IL-1β mRNA synthesis (median of 10,044 copies), and could be clearly distinguished (P=0.005) from tissues with diffuse infiltrates, which had a low level transcription. The results for TNF-α paralleled the findings for IL-1β ($r^2$=0.860; P<0.001; FIG. 2). A low copy number (median of 660 copies) was found in diffusely infiltrated tissue compared with an intermediate level of TNF-α transcription in follicular tissue (median of 1799 copies; P=0.04) and high concentrations in granulomatous synovitis (median of 9568 copies; P=0.005).

Low, intermediate, and high IL-1β and TNF-α production correlated with IFN-γ transcription in all three disease variants ($r^2$=0.674 and P<0.001 for IL-1β and $r^2$=0.607 and P<0.001 for TNF-α compared to IFN-γ). This relationship is compatible with a regulatory role of the T cell product, IFN-γ, in macrophage activation. In this model, rheumatoid granulomas could be regarded as sites of marked T cell and macrophage stimulation. The histiocyte formation characteristic of the granulomas would be consistent with this hypothesis.

Example 4

Anti-Inflammatory Cytokines in District Variants of Rheumatoid Synovitis

The concentrations of IL-10 and TGF-β1 mRNA in the tissues were semiquantified.

Figure 3:
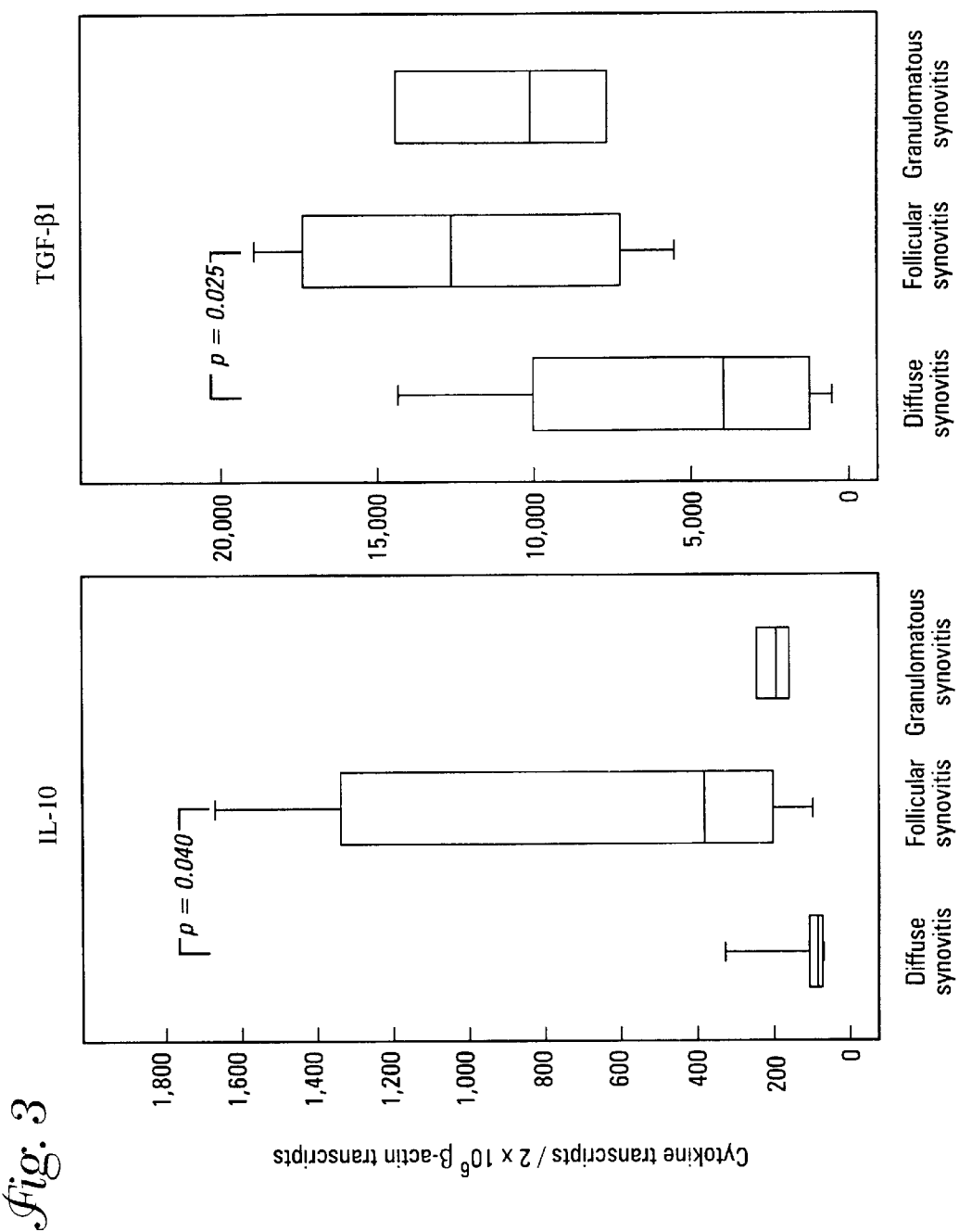
FIG. 3 contains two bar graphs plotting the number of cytokine transcripts (IL-10 and TGF-β1) per β-actin transcripts for diffuse, follicular, and granulomatous synovial tissues.

IL-10 transcripts were consistently found (FIG. 3). The lowest tissue concentration of IL-10 mRNA correlated with the presence of diffuse synovitis. In these patients, the median copy numbers of cytokine per $2 \times 10^6$ β-actin sequences was 76. In contrast, abundance of IL-10 transcripts was a characteristic feature of follicular synovitis. Patients with follicular aggregates synthesized a median of 331 copies of IL-10-specific sequences (P=0.04). Despite the marked stimulation of macrophages in the granulomatous synovitis, IL-10 was present at only low levels (median of 181 copies). Although macrophages are the main producer of IL-10 in the inflamed synovium, macrophage stimulation as indicated by IL-1β production can thus be differentiated from IL-10 production.

TGF-β1 is understood as a powerful suppressive cytokine. To explore whether the subdued production of T cell and macrophage products in the diffuse synovitis was correlated with a dominance of TGF-β1 mRNA, this cytokine was analyzed in all three variants of rheumatoid synovitis. TGF-β1 sequences could easily be detected in all but one patient. Transcript concentrations ranged from 0 to 19,020 copies (FIG. 3). Low levels of TGF-β1 transcription was a common denominator among patients with diffuse synovitis. They synthesized a median of 3901 copies, a finding that distinguished them from patients with follicular disease (median of 12,636 copies; P=0.025).

Therefore, neither IL-10 nor TGF-β1 could account for the aborted cytokine response in diffuse synovitis. IL-10, so far recognized as a suppressive cytokine, was transcribed in tissue samples with follicular T-B aggregates and was distinctly low in granulomatous synovitis whereas TGF-β1 mRNA was found in all three forms of synovitis.

Example 5

Host Factors Correlate with the Organization and Function of Inflammatory Cells in the Rheumatoid Synovium Results on tissue cytokine pattern suggested that more than one type of rheumatoid synovitis exists with distinct pathways of inflammation. Phenotypic heterogeneity of RA could be attributed to differences in host factors. To address this issue, the three patient subsets were compared for demographic features and for similarities in clinical presentation. Also, it could be argued that differences in the histopathological appearance and functional profiles of accumulated cells could be influenced by therapeutic intervention. Treatment given in the last few weeks before harvesting of the tissue could be particularly important in affecting the disease process in the synovial membrane.

The demographic characteristics of the patient cohorts stratified according to the histomorphology of the synovitis are presented in Table 3. Sex, age, and disease duration did not predict which variant of synovitis the patient had developed. All patients had long-standing disease, but no differences were seen that correlated with a specific organizational and functional pattern in the tissue. Patients lacking rheumatoid factor production accumulated among the cohort of individuals found to have diffuse synovitis. The group of patients with diffuse synovitis included in five of ten patients who were seronegative, whereas all patients who had developed follicular synovitis secreted rheumatoid factor (P=0.04). The most intriguing finding was that the generation of the rheumatoid nodules was characteristic for individuals with synovial granuloma formation. All patients with granulomatous synovitis, but none of the patients with follicular synovitis and only one of ten patients with diffuse synovitis, had rheumatoid nodules of the skin. The accumulation of patients with nodular disease in the category of granulomatous synovitis was statistically significant (P=0.005 versus diffuse synovitis; P=0.003 versus follicular synovitis). Pertinent treatment information is summarized in Table 4. All individuals with granulomatous synovitis had been treated with disease-modifying agents (DMARDs) such as hydroxychloroquine, steroids, gold, sulphasalazine, azothioprine, and methotrexate. None of these patients had been managed with nonsteroidal anti-inflammatory drugs (NSAIDs) alone. The group of patients with diffuse synovitis appeared to have been treated less aggressively. One-third of these patients was managed with NSAIDs only. All patients with granuloma formation in the synovia, but only 30 and 29%, respectively, of patients in the diffuse and follicular categories, were on methotrexate. Despite the low number of individuals analyzed, these differences showed a trend toward significance (P=0.07 and P=0.06, respectively). This analysis suggested that host factors and/or treatment may contribute to the microanatomy in the joint or vice versa (i.e., that a correlation exists between systemic manifestations and certain types of rheumatoid synovitis).

TABLE 3

Characteristics of Patient Populations Defined by Histopathological Patterns

| | Sex (♀/♂) | Median age in years (range) | Median disease duration in years (range) | Rheumatoid factor positive* | Rheumatoid nodules** |
|---|---|---|---|---|---|
| Diffuse synovitis | 5/5 | 57 (52–73) | 16.5 (1–51) | 50% | 10% |
| Follicular synovitis | 6/1 | 57 (34–67) | 10 (4–50) | 100% | 0% |
| Granulomatous synovitis | 3/1 | 61.5 (24–68) | 8 (5–32) | 75% | 100% |

*P = 0.004 for diffuse versus follicular synovitis.
**P = 0.005 for diffuse versus granulomatous and P = 0.003 for follicular versus granulomatous synovitis.
All other comparisons were nonsignificant.

TABLE 4

Past and Current Treatment in the Different Patient Categories

| | Diffuse synovitis (A) | Follicular synovitis (B) | Granulomatous synovitis (C) | A vs B | A vs C | B vs C |
|---|---|---|---|---|---|---|
| NSAID only (last 3 months before surgery) | 4/10 | 1/7 | 0/4 | NS | NS | NS |
| DMARD (last 3 months before surgery) | 6/10 | 6/7 | 4/4 | NS | NS | NS |
| Methotrexate (last 3 months before surgery) | 3/10 | 2/7 | 4/4 | NS | 0.07 | 0.06 |
| DMARD (total) | 7/10 | 6/7 | 4/4 | NS | NS | NS |

NSAID, nonsteroidal anti-inflammatory drugs; DMARD, disease-modifying anti-rheumatic drugs; NS, not significant.

Example 6

Tissue Cytokine Patterns Distinguish Variants of RA

RA is a chronic inflammatory disease with profound phenotypic variability (Harris E D (ed): Rheumatoid Arthritis. Philadelphia, WB Saunders Co., pp.3–212 (1997)). The pattern of involvement, the course and destructive potential of the disease, and the frequency of extra-articular manifestations vary significantly. Reasons for the phenotypic heterogeneity are not completely understood but may include variable combinations of disease risk genes (Ollier W E, MacGregor A: Br Med Bull, pp.51:267–285 (1995); and Weyand C M, Goronzy J J: *Med Clin North Am*, pp.81:29–55 (1997)). The results presented herein indicate that the heterogeneity of the disease process includes the synovial lesion and that patients display considerable differences in the organization and the functional commitment of the inflammatory infiltrates. The microanatomy of the inflamed synovium showed a correlation with profiles of tissue cytokines, supporting the model that different mechanisms are functional in regulating rheumatoid synovitis. Tissue destruction and possible other aspects of the disease process are related to cell-cell interactions in the infiltrates. Thus, understanding the rules underlying the emergence of a defined microanatomical structure in the synovial membrane provides information about the fundamentally important pathological events leading up to RA.

The results from the study presented herein indicate that the topographical arrangement of the mononuclear infiltrate can be used to define three variants of rheumatoid synovitis. These three patterns correlated with the combination and the amount of cytokines produced in the tissue. In general, the level of transcription of T-cell derived cytokines is low in synovial tissue, and the study thus employed a semiquantitative PCR approach. This technique can have limitations that need to be considered when interpreting the data. As it is a semiquantitative method, differences have to be large to be distinguished. Also, the level of cytokine mRNA may not necessarily reflect the amount of functionally active protein, particularly in the case of TGF-$\beta$1 and IL-1$\beta$. Cytokine production was confirmed by immunohistochemistry, which, however, is not a suitable technique to determine quantitative differences. The finding that 21 samples were sufficient to accomplish a dissection of the three variants emphasizes that the differences in cytokine production were pronounced.

The first variant of RA emerging from the study is a disease phenotype characterized by diffuse infiltrates in the synovia, a lower probability of rheumatoid factor production, and a clinically milder disease that is responsive to nonaggressive treatment. The low transcription of proinflammatory mediators of a $T_H0$ pattern suggested that the T cell response was not highly differentiated. Consistent with the interpretation is the absence of a microatomical organization of the mononuclear infiltrate. The reason for this subdued activation of inflammatory cells is unclear. Production of the anti-inflammatory cytokines IL-10 and TGF-$\beta$ were generally low, and no evidence was found for an activate suppressive mechanism.

The second variant of RA distinguished in this study represents the histomorphological pattern that is typically associated with RA, the formation of follicular structures composed of T and B cells. Recent molecular characterization of B cells isolated from RA tissues with follicular centers have confirmed that these T-B cell aggregates functionally resemble germinal centers (Schroeder, et al., *Proc Natl Acad Sci USA*, pp.93:221–225 (1996); and Randen, et al., *Scan J Immunol*, pp.41:481–486(1995)). Germinal centers are the site of B cell differentiation, somatic mutation, and affinity maturation, all of which are T-cell-dependent processes.

The tissue cytokine profile that emerged for this category included intermediate levels of IFN-$\gamma$ with essentially absent IL-4 transcription. This pattern would suggest a $T_H1$ deviation of the immune response. The predominance of a $T_H1$ pattern in patients with follicular synovitis is in line with current knowledge in cytokine production in germinal centers (Kelsoe G: *Semin Immunol*, pp.8:179–184)). Although IL-4 deficient mice generated by gene targeting are not able to form lymphoid follicles (Kuhn, et al., *Science*, pp.254:707–710 (1991)), T cells accumulating in germinal centers typically do not produce IL-4 but IFN-$\gamma$. Also the production of IL-10 found in the tissues with follicular aggregates may relate to germinal center formation (Levy Y, Brouet J C, *J Clin Invest*, pp.93:424–428)). IL-10 can be produced by a variety of cells, including $T_H1$ and $T_H2$ type T-cells, macrophages, and B cells. It acts by inhibiting the production of numerous pro-inflammatory monokines and be attenuating $T_H1$ mediated immune responses. In contrast to this immunosuppressive effect, IL-10 as marked stimulatory effects on B cells and supports B cell proliferation and differentiation. In particular, the production of rheumatoid factor appears to be IL-10 dependent (Perez, et al., *Arthritis Rheum*, pp.38:1771–1776 (1995). The data herein would suggest that the production of IL-10 in follicular synovitis relates to providing a microenvironment for B cell proliferation and not for suppressing macrophage activation.

The third variant of RA identified in this study was the least frequent and was characterized by the most abundant production of T-cell- and macrophage-derived cytokines. From a clinical perspective, granulomatous synovitis occurred in patients with the most serious presentation of the disease, extra-articular RA. The morphological structures encountered in the synovia resembled rheumatoid nodules, which are usually found in the skin (i.e., subcutaneous nodules). Unexpectedly, granulomatous and follicular synovitis did not co-occur and follicular structures were distinctly absent from the rheumatoid nodules. In addition, the cytokine profiles correlating with the two histomorphologies were distinct. Granulomatous disease was characterized by high production of IFN-$\gamma$, IL-4, IL-1$\beta$, and TNF-$\alpha$ whereas the follicular disease resembled a classical $T_H1$ response with the virtual absence of IL-4.

The co-production of IFN-$\gamma$ and IL-4 is unusual for a granulomatous reaction. Participation of cytokines in granuloma formation has been studied under various experimental conditions. In general, hypersensitivity granuloma (in contrast to the nonimmune foreign-body-type lesions) represents a chronic inflammatory infiltrate of macrophages, in particular, epithelioid macrophages, multinucleated giant cells and T cells (Boros D L, *Prog Allergy*, pp.24:183–267 (1978)). The two most widely used experimental systems are mycobacteria- and schistosoma-egg-induced granuloma formation. In these two systems, granuloma formation has been associated with quite distinct patterns of tissue cytokines. The mycobacteria-induced lesion is a characteristic $T_H1$ response, with predominantly IFN-$\gamma$ at the site of inflammation (Barnes, et al., *J Immunol*, pp.145:149–154 (1990)). In addition to IFN-$\gamma$, TNF-$\alpha$ has been found to be critical in the granuloma formation during bacile Calmette Guerin (BCG) infection (Kindler, et al., *Cell*, pp.56:731–740 (1989)). Because IFN-$\gamma$ is known to augment TNF production, it is likely to be a critical mediator in granuloma formation. A similar cytokine pattern is seen in the chronic inflammation of giant cell arteritis, which is also characterized by granuloma formation (Weyand, et al., *Ann Intern Med*, pp.121:484–491(1994)). In contrast, the schistosoma-egg-induced granuloma is characterized by a $T_H2$ type response with the prominent production of IL-4, IL-5, and IL-10 (Grzych, et al., *J Immunol*, pp.146:1322–1327 (1991); and Chensue, et al., *J Immunol*, pp.148:900–906(1992)). How $T_H2$ derived cytokines, in particular IL-4, participate in this type of granuloma formation is not entirely clear. For example, it is not understood what the macrophage-activating agent in this type of lesion is. Nevertheless, $T_H1$ as well as $T_H2$ associated cytokines can apparently participate in granuloma formation.

The granuloma formation in the rheumatoid synovium was different from these experimental models in that IFN-γ and IL-4 were co-produced. Previous results have emphasized their antagonistic effects (Seder R A, Paul W E: *Annu Rev Immunol*, pp.12:635–673 (1994); Abbas, et al., *Nature*, pp.383:787–793 (1996); Seder, et al., *J Exp Med*, pp.176:1091–1098 (1992); Seder, et al., *Proc Natl Acad Sci USA*, pp.90:10199–10192 (1993); and Szabo, et al., *J Exp Med*, pp.185:817–824 (1997)). Neutralization of IFN-γ production enhances granuloma formation in the schistosoma model although it abrogates the inflammation in the microbacterial model. However, it is possible that these findings are restricted to the early stages of granuloma formation and many not apply to chronic inflammation, as is the case in the rheumatoid synovium. Indeed, a temporal participation of $T_H1$ as well $T_H2$ cells has been described for the mycobacterial infection as well as for the schistosoma-egg-induced granuloma (Boros D L, *Immunobiology*, pp.191:441–450 (1994); Chensue, et al., *J Immunol*, pp.151:1391–1400 (1993); and Orme, et al., *J Immunol*, pp.151:518–525 (1993)).

The data presented herein indicate the contribution of different cytokines in controlling the microanatomy of the synovial inflammation and also emphasize the necessity to re-evaluate the role of the immune pathways in the pathogenesis of RA. Immune deviation is now widely accepted as a concept in explaining the pathogenesis of autoimmune diseases. This model implies that chronic inflammation is a consequence of the aberrant commitment to an immune pathway in response to a given antigen (Finkelman F D, *J Exp Med*, pp.182:279–282 (1995). Studies in diseases such as infection with leishmania major and mycobacterium leprae have fueled the hypothesis that immune reactions to a given antigen can take very different paths, and accordingly, a certain type of disease may develop (Heinzel, et al., *J Exp Med*, pp.169:59–72 (1989); Yamamura, et al., *Science*, pp.254:277–279 (1991)). Tuberculoid leprosy and lepratomatous leprosy have been distinguished as two disease phenotypes, the distinction being mainly attributed to the involvement of different cytokine networks. Following this model, RA has been considered a consequence of an immune deviation toward a $T_H1$ response, and the use of IL-4 and IL-10 have been proposed as therapeutic interventions (Heinzel, et al., *J Exp Med*, pp.169:59–72 (1989); Yamamura, et al., *Science*, pp.254:277–279 (1991); Simon, et al., *Proc Natl Acad Sci USA*, pp.91:8562–8566, (1994); Van Roon, et al., *Arthritis Rheum*, pp.39:829–835 (1996); Isomaki, et al., *Arthritis Rheum*, pp.39:386–395 (1996); Walmsley, et al., *Arthritis Rheum*, pp.39:495–503 (1996)). The present finding that RA encompasses different cytokine patterns indicates that the choices of the host in terms of cytokine recruitment do not determine whether or not the individual develops the disease but can influence disease severity and organ involvement.

Alternatively, the three disease phenotypes may reflect distinct pathomechanisms including different disease initiators. As the initial events in RA are not understood, both models remain feasible. However, searches into the instigators of RA could benefit from the realization that there exist several variants of the disease. It might be misleading to search for common denominators in a cohort of RA patients if multiple distinct disease variants are represented. Focusing on a single entity of RA may enhance the identification of the shared pathomechanisms, genetic risk factors, and antigens driving rheumatoid synovitis. Equally important, phenotypic variants of RA should be considered in the design of treatment trials and in the application of therapeutic agents in individual patients.

In summary, RA is a chronic inflammatory disease with primary manifestations in the synovial membrane. Tissue infiltrates are composed of T cells, B cells, and macrophages, but histopathological appearances vary widely and rarely pathognomonic. Mechanisms underlying the phenotypic heterogeneity of rheumatoid arthritis are not known. To explore whether a correlation exists between the microscopic patterns of rheumatoid synovitis and in situ production of cytokines, tissue samples from 21 consecutive patients with clinically advanced active RA were examined. Based upon the organization of the lymphocyte infiltrate, the synovial biopsies were categorized into three distinct subsets. Ten samples were characterized by diffuse lymphoid infiltrates without further microarrangements. In seven samples, lymphoid follicles with germinal center formation were detected, and in four specimens, granuloma formation was identified. In all specimens, cytokine transcription of interferon (IFN)-γ, interleukin (IL)-4, IL-1β, tumor necrosis factor (TNF)-α, IL-10, and transforming growth factor-β1 was semiquantified with polymerase chain reaction and liquid phase hybridization. Each of the morphologically defined variants of synovitis displayed a unique cytokine profile. Low-level transcription of IFN-γ, IL-4, IL-1β, and TNF-α was typical of diffuse synovitis. In follicular synovitis, IFN-γ was the dominant cytokine, IL-4 was virtually undetectable, and IL-10 was abundant. Granulomatous synovitis demonstrated high transcription of IFN-γ, IL-4, IL-1β, and TNF-α and could be clearly distinguished from the other phenotypes. To investigate whether differences in the synovial lesions were related to host factors, patients were compared for clinical parameters. Diffuse synovitis was seen in most of the patients with seronegative RA, the mildest form of the disease. In contrast, extraarticular spreading of RA with nodule formation was typically associated with granulomatous synovitis.

Example 7

HLA-DRB1 Alleles Associated with RA

1. The Shared Epitope Hypothesis

The association of RA to MHC class II genes was recognized in the 1970s and provided the framework for an important disease model (Rittner, et al., *Mol Med* 3:452 (1997)). Sharing of MHC class II alleles in RA patients was taken as evidence that the major biological function of these molecules, the presentation of antigenic peptides to T cells, was critically involved in disease pathogenesis (Todd, et al., *Science* 240:1003 (1988)). A widely accepted paradigm holds that RA represents the sequel of pathologic T cell responses initiated and maintained by antigens presented in the context of disease-associated HLA molecules. The initial observation that the frequency of HLA-DR4 was increased in RA patients was confirmed in multiple studies and in multiple ethnic groups. The association with HLA-DR4 was eventually attributed to some of the allelic variants of the HLA-DR4 family, including HLA-DRB1*0401, *0404, *0405, and *0408 (Table 5). Sequence similarity between these disease-associated alleles and the sequence differences to the nonassociated allele HLA-DRB1*0402 gave rise to the "shared epitope" hypothesis (Gregersen, et al., *Arthritis Rheum* 30:1205 (1987); Nepom, et al., *Annu Rev Immunol* 9:493 (1991); and Winchester R., *Adv Immunol* 56:389 (1994)). This shared sequence stretch was also identified in HLA-DRB1*01 alleles enriched in Jewish patients with RA and in the HLA-DRB1*1402 allele in Yakima Indians (Willkens, et al., *Arthritis Rheum* 34:43 (1991); and Willkens, et al., *Arthritis Rheum* 34:43 (1991)). The "shared epitope" hypothesis emerged as a unifying model of the HLA-DR association of RA, and it suggested a direct involvement of a sequence motif spanning positions 67–74 of the HLA-DRB1 gene in the pathogenesis of RA. Numerous studies have tested the shared epitope hypothesis in patients with different ethnic backgrounds and have provided evidence for an over representation of a set of HLA-DRB1 alleles that share sequence similarities in the third hypervariable region of the DRB1 gene (Weyand, et al., *Curr Opin Rheumatol* 7:206 (1995); and Winchester R., *Adv Immunol* 56:389 (1994). It has been emphasized that all RA-associated alleles exhibit a preference for positively charged amino acids at positions 70 and 71, but sequence variations in these two positions among RA-associated alleles have been believed to be of limited functional importance. Also, the role of sequence polymorphisms at positions 67 and 74 is not understood. HLA-DRB1 *0403, which differs from the "shared epitope" alleles at position 74, is frequently found in Hispanic patients, opening the possibility that considerable variability is encountered in the amino acids forming the "shared epitope."

Resolution of the crystal structure of HLA-DR molecules has allowed for the precise localization of the "shared epitope." Amino acid positions 70, 71, 74, and 78 have been shown to surround peptide binding pocket 4 (Brown, et al., *Nature* 364:33 (1993); and Stern, et al., *Nature* 368:215 (1994)). The mapping of the disease-associated sequence stretch to the antigen binding groove emphasizes a role for antigen selection, binding, and presentation in RA. Indeed, the positive charge at position 71 favors the selection of peptides with a negative charge to this position (Hammer, et al., *J Exp Med* 181:1847 (1995)). Dessen et al. have determined the x-ray structure of HLA-DR4 (DRB1 *0401) complexed with a human type II collagen peptide (1168–1180) and have described hydrogen bonds between the Lys in position 71 of the HLA-DRβ1 chain and both the main carbonyl oxygen of the Asn and the Asp side chain at positions 4 and 5 of the peptide, respectively (Dessen, et al., *Immunity* 7:473 (1997)).

While these studies have greatly improved our understanding about peptide-HLA interaction, they have also raised several questions that remain unanswered. How likely is it that the same peptides are bound by HLA molecules that display similarities in some of the amino acid positions in binding pocket 4, and can we indeed ignore the sequence variations inside and outside of the shared epitope? There are notable allelic differences between RA-associated alleles that influence the binding properties of several HLA-DR pockets, but these are not considered to be critical for the disease association. Disease-associated HLA-DR4 variants have either a Val or a Gly at position 86. This dimorphism has a major impact on T cell recognition, probably by altering the specificity of peptide binding pocket 1 (Fu, et al., *J Exp Med* 181:915 (1991)). The collagen peptide crystallized with HLA-DRB1 *0401 has a Met in position 1 and is therefore unlikely to bind to HLA-DRB1 *0404. Also, the size of pocket 4 is smaller in DRB1 *0404/8 (Arg at position 71) than in DRB1 *0401 (Lys at position 71). Sequence polymorphisms in HLA-DR1 alleles add additional complexity. Amino acids at position 13, which are different in HLA-DR1 and HLA-DR4, contribute to binding pocket 4. Pocket 6 is deeper in DR4 than in DR1 because of the smaller side chan of Val in DR4 at position 11 compared with the Leu in DR1. In contrast, a Tyr versus Ser exchange at position 30 reduces the size of pocket 7 in DR4 in comparison with DR1. Additional different binding properties can be predicted for other disease-associated HLA-DRB1 alleles, such as DRB1 *1402 and *1001.

Alternatively, models have been proposed to explain the sharing of a sequence polymorphism of the HLA-DRB1 molecule in RA. Carson et al. have favored the hypothesis that the peptide encoded by the shared epitope is recognized as a self-antigen and may therefore influence thymic selection (Roudier, et al., *Proc Natl Acad Sci USA* 86:5104 (1989)). Support for this model has come from subsequent studies demonstrating that HLA-DR-derived peptides can be presented in restriction to HLA-DQ (Salvat, et al., *J Immunol* 153:5321 (1994)). Albani and Carson have shown that the recognition of microbial peptides expressing sequence homologies to the shared epitope is altered in RA patients (Albani, et al., *Immunol Today* 17:466 (1996)). Based on these data, this group has developed a molecular mimicry model of RA in which positive selection in the thymus favors T cells that cross-react between microbial and self-antigens (Albani, et al., *Nat Med* 1:448 (1995)). An alternative hypothesis has been proposed by David et al. who also predict a role of HLA-DR-derived peptides in thymic selection (Taneja, et al., *J Clin Invest* 101:921 (1998)). They, however, have postulated that peptides derived from non-associated HLA-DR molecules, and not from disease-associated molecules, are functionally important and that these peptides somehow select regulatory T cells that protect against collagen-induced arthritis.

Finally, it is possible that the shared epitope functions in RA by directly contacting the TCR molecule. This model has been originally proposed based on response patterns and TCR BV gene segment usage of alloreactive T cell clones and the mapping of antibody binding sites on the HLA-DRβ1 chain by site-directed mutagenesis (Goronzy, et al., *Rheum Dis Clin North Am* 21:655 (1995); Hiraiwa, et al., *Proc Natl Acad Sci USA* 87:8051 (1990); and Weyand, et al., *Arthritis Rheum* 37:514 (1994)). More recently, the crystal structure of HLA-DR peptide complexes has confirmed that amino acids at position 70 of the HLA-DRβ1 chain project out of the binding site and may directly interact with the TCR (Dessen, et al., *Immunity* 7:473 (1997); and Stern, et al., *Nature* 368:215 (1994)). Penzotti et al. (*Arthritis Rheum* 40:1316 (1997)) have modeled a TCR from an HLA-DR4-specific clone and the DRB1 *0404 molecule and have predicted that TCR residues CDR1β Asp30, CDR2β Asn51, and CDR3β Gln97 are positioned to participate in hydrostatic interactions with the DRB1 residues Q and R at positions 70 and 71, respectively, of the shared epitope. These contact residues are likely important in repertoire selection. Indeed, the RA-associated HLA-DR polymorphism has been found to induce global repertoire changes that are reflected at the level of TCR BV-BJ gene segment frequencies (Walser-Kuntz, et al., *Immunity* 2:597 (1995)). In particular, TCRs were affected that had a consensus Gly-Pro-Gly sequence and therefore were predicted to have a more rigid structure.

TABLE 5

HLA-DR association of RA

| Serotype | Cellular type | Genotype | Disease association |
|---|---|---|---|
| HLA-DR4 | HLA-Dw4 | HLA-DRB1 *0401 | + |
|  | HLA-Dw10 | HLA-DRB1 *0402 | − |
|  | HLA-Dw13 | HLA-DRB1 *0403 | − |
|  |  | HLA-DRB1 *0407 | − |
|  | HLA-Dw14 | HLA-DRB1 *0404 | + |
|  |  | HLA-DRB1 *0408 | + |
|  | HLA-Dw15 | HLA-DRB1 *0405 | + |

TABLE 5-continued

HLA-DR association of RA

| Serotype | Cellular type | Genotype | Disease association |
| --- | --- | --- | --- |
| HLA-DR1 | HLA-Dw1 | HLA-DRB1 *0101 | + |
| HLA-DRw6 | HLA-Dw9 | HLA-DRB1 *1401 | − |
| | HLA-Dw16 | HLA-DRB1 *1402 | + |
| | HLA-Dw18 | HLA-DRB1 *1301 | − |
| | HLA-Dw19 | HLA-DRB1 *1302 | − |

2. The Alternative View—A "Multiple HLA Polymorphisms—Multiple Disease Variants" Model The HLA-DR association of RA has been studied in many ethnic groups, and all disease-associated alleles defined so far, express the "shared epitope." While this observation suggests a common denominator and a single pathomechanism underlying the HLA association of RA, several aspects of these studies require a rethinking of such a simplified model. First, it should be noted that the strength of the association is not uniform but varies widely depending on the ethnic background of the patients. Second, not all shared-epitope alleles are equal, for example, HLA-DRB1*0401 may have an exceptional role.

Indications that this genetic heterogeneity may be useful in dissecting the clinical heterogeneity of RA came from association studies in Caucasian patients stratified for different disease manifestations (Weyand, et al., Ann Intern Med 117:801 (1992); and Weyand, et al., J Clin Invest 89:2033 (1992)). Earlier studies had indicated that HLA-DR4 may be associated with more erosive disease (Olsen, et al., Am J Med 84:257 (1988)). Subsequent studies showed that patients with rheumatoid factor (RF)-negative (seronegative) RA were characterized by an enrichment of both the HLA-DRB1 *04 and *01 alleles (Weyand, et al., J Clin Invest 95:2120 (1995)). In contrast, 90% of patients with erosive seropositive disease had at least one copy of an HLA-DRB1 *04 allele. Sequence analysis of HLA-DRB1 *04 genes in the seronegative cohort identified the DRB1 *0404 and B1 *0408 variants as the dominant alleles. This contrasted to the overrepresentation of B1 *0401 in the seropositive patients. Clinical dissection of the seronegative patients demonstrated that erosive disease occurred more frequently in the HLA-DRB1 *04-positive individuals. A similar correlation between the inheritance of HLA-DRB1 alleles and the severity of joint destruction emerged for patients with seropositive RA. While all of these patients had erosive disease, patients carrying two disease-associated alleles, either HLA-DRB1*01/04 or HLA-DRB1*04/04, had a higher frequency of joint arthroplasty (Weyand, et al., Ann Intern Med 117:801 (1992)). Based on these observation, it is now proposed that there is a hierarchy of HLA-DRB1 polymorphisms determining the severity of joint inflammation. This model would imply that the disease-associated HLA-DRB1 polymorphism is not only functioning in disease initiation but also in disease progression. As described herein, HLA-DRB1 typing can be used as a prognostic marker to predict disease severity.

An alternative approach would suggest that the clinical phenotypes of RA are not simply steps on a severity scale. Rather, they could be viewed as distinct entities of the disease with ultimately unique pathogeneses. Disease-associated HLA-DRB1 alleles, in spite of sharing a similar sequence stretch, may differ in their contribution to the disease. This model also includes that more than one inflammatory pathway can lead to synovitis and that the clinical category of polyarthritis is a "mixed bag" with multiple forms of inflammation. Assigning different genotypes to different types of RA also provides an explanation for the finding that the strength of association between HLA-DR4 and disease is not maintained in all populations. The majority of African-American patients lack HLA-DR4 (McDaniel, et al., Ann Intern Med 123:181 (1995)). While this finding could raise the question whether HLA class II molecules are a prerequisite in the pathological events typical for the disease, it could also be interpreted as demonstrating fundamental differences in the disease processes leading to symmetrical polyarthritis in Caucasians and African-Americans. Similar considerations could be applied to population-based studies describing a lack of association with HLA-DR4 in patients diagnosed with symmetric polyarthritis.

Some clinical observations reinforce that the different disease patterns encountered in RA may actually represent different entities. Impressive discrepancies in the disease course of synovial inflammation and extra-articular RA are compatible with independent disease mechanisms in these two different dimensions of RA. Major organ manifestations frequently occur in RA patients at times when the synovial disease is quiescent. In selected patients, rheumatoid nodules involving the skin or other organs can be induced by methotrexate although the treatment successfully controls synovial inflammation (Merrill, et al., Arthritis Rheum 40:1308 (1997)). Rheumatoid nodules impress histomorphologically as a granulomatous reaction, distinct from the inflammatory lesions of rheumatoid synovitis. It has, therefore, been suggested that extra-articular disease is a different dimension of RA with different pathomechanisms and not just a more severe form of the disease. In Caucasians, major organ involvement is essentially restricted to patients who bear HLA-DR4 and it is generally not seen in patients who express only one of the other disease-associated alleles, again emphasizing the unique role of the HLA-DR4 haplotype. Even more striking is a gene-dose effect in patients with extra-articular manifestations. Patients with erosive RF-positive joint disease are characterized by the genotype HLA-DRB1*04/x (x represents an RA non-associated allele). In contrast, nodule formation is a hallmark of patients with the genotypes DRB1*01/04 or DRB1*0401/0404 (Weyand, et al., J Clin Invest 89:2033 (1992)). Homozygosity for DRB1*0401 is a strong predictor for rheumatoid vasculitis and Felty's syndrome (Lanchbury, et al., Hum Immunol 32:56 (1991); and Weyand, et al., J Clin Invest 89:2033 (1992)) both of which are severe complications of RA associated with significant morbidity and mortality. The importance of a gene-dose effect in extra-articular disease does not necessarily imply an additive effect of RA-associated HLA alleles on a severity scale. A synergistic interaction between the two haplotypes is a more likely scenario. In this model, the functional role of HLA-DRB1 alleles in synovial and extra articular disease is regarded as distinct, e.g., peptide selection in synovitis and repertoire formation in extra-articular disease.

In summary, the diagnostic category of RA is an umbrella term that encompasses multiple subtypes, each of which is associated with different HLA-DR polymorphisms. As the heterogeneity of the disease should have a major impact on disease course and therapeutic responsiveness, HLA-DR molecules could be used to dissect the crude category of RA into pathogenically homogeneous subsets.

3. Patient Population and HLA-DRB1 Genotyping

The HLA-DRB1 genotype of patients classified as having a diffuse, follicular, or granulomatous phenotype was determined using PCR according to the methods and materials provided by One Lambda (Los Angles, Calif.) or Biotest Diagnostics (Denville, N.J.).

Example 8

Disease Phenotypes in RA and Genetic Control of T Cell Function

Additional evidence for distinct pathomechanisms in different forms of RA has come from studies of abnormal T cell functions in RA. Several lines of evidence have implicated T cells as important players in RA pathogenesis. The MHC class II association has emphasized the critical role of TCR-MHC interactions in the pathogenesis of the disease (Winchester R., *Adv Immunol* 56:389 (1994)). Equally important is the histomorphology of rheumatoid synovitis, which points to T cells as relevant component of pathogenic events. Inflammatory lesions in the synovial membrane are composed of T cells, macrophages, B cells, and synoviocytes. Notably, these inflammatory cells acquire distinct topographic arrangements of which follicular T cell-B cell aggregates are the most interesting (Kurosaka, et al., *J Exp Med* 158:1191 (1983)). Follicular structures in rheumatoid synovitis display morphologic, phenotypic, and functional characteristics resembling germinal centers (Schroder, et al., *Proc Natl Acad Sci USA* 93:221 (1996)). The formation of germinal centers, usually restricted to lymphoid organs, is a T cell dependent process and provides a unique microenvironment for the generation of high affinity B cell responses. Most T cell studies in RA have therefore focused on identifying and characterizing the TCRs that might recognize antigen in the synovial tissue. Repertoire analysis of synovial T cells have demonstrated that the infiltrate is heterogeneous, that some T cells are clonally expanded, and that different T cells are dominant in different patients. These studies have emphasized the heterogeneity of the disease process without defining a common denominator. Relatively few studies have attempted to identify variables of T cell function that might be genetically determined and reflect disease-risk genes. Allelic polymorphisms of TCR genes have received the greatest attention, but these studies have remained inconclusive (Cornelis, et al., *Arthritis Rheum* 40:1387(1997); and Hall, et al., *Arthritis Rheum* 40:1798 (1997)). More recent data, however, indicate that abnormalities in the T cell repertoire and some unexpected T cell functions in RA have a genetic basis and correlate with the clinical expression of RA.

Figure 4:
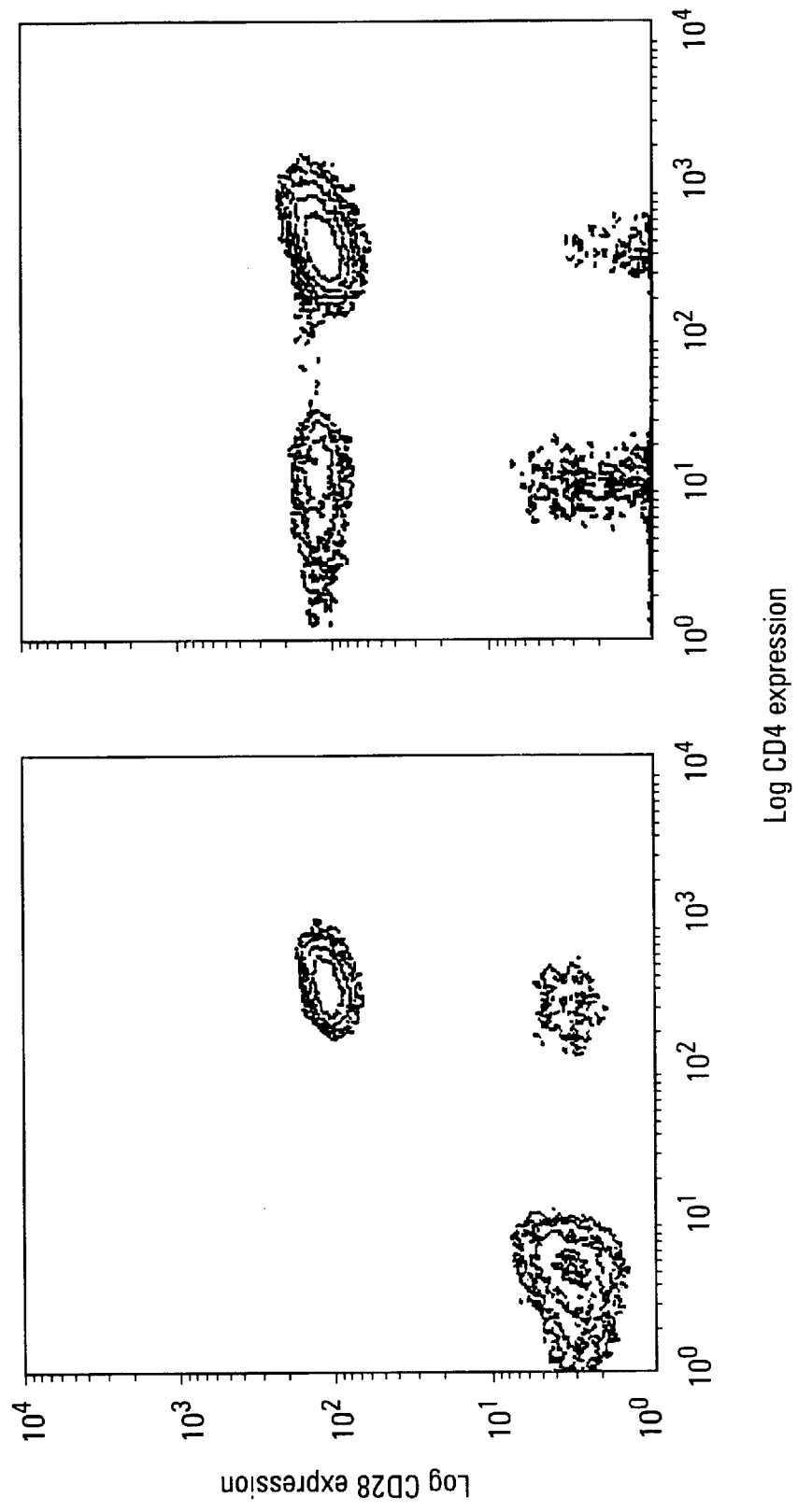
FIG. 4 contains two graphs plotting CD28 expression against CD4 expression for a normal control individual (left, <1% of $CD4^+$ T cells are CD28 negative) and a RA patient (right, about 9% of $CD4^+$ T cells are CD28 negative).
Figure 5:
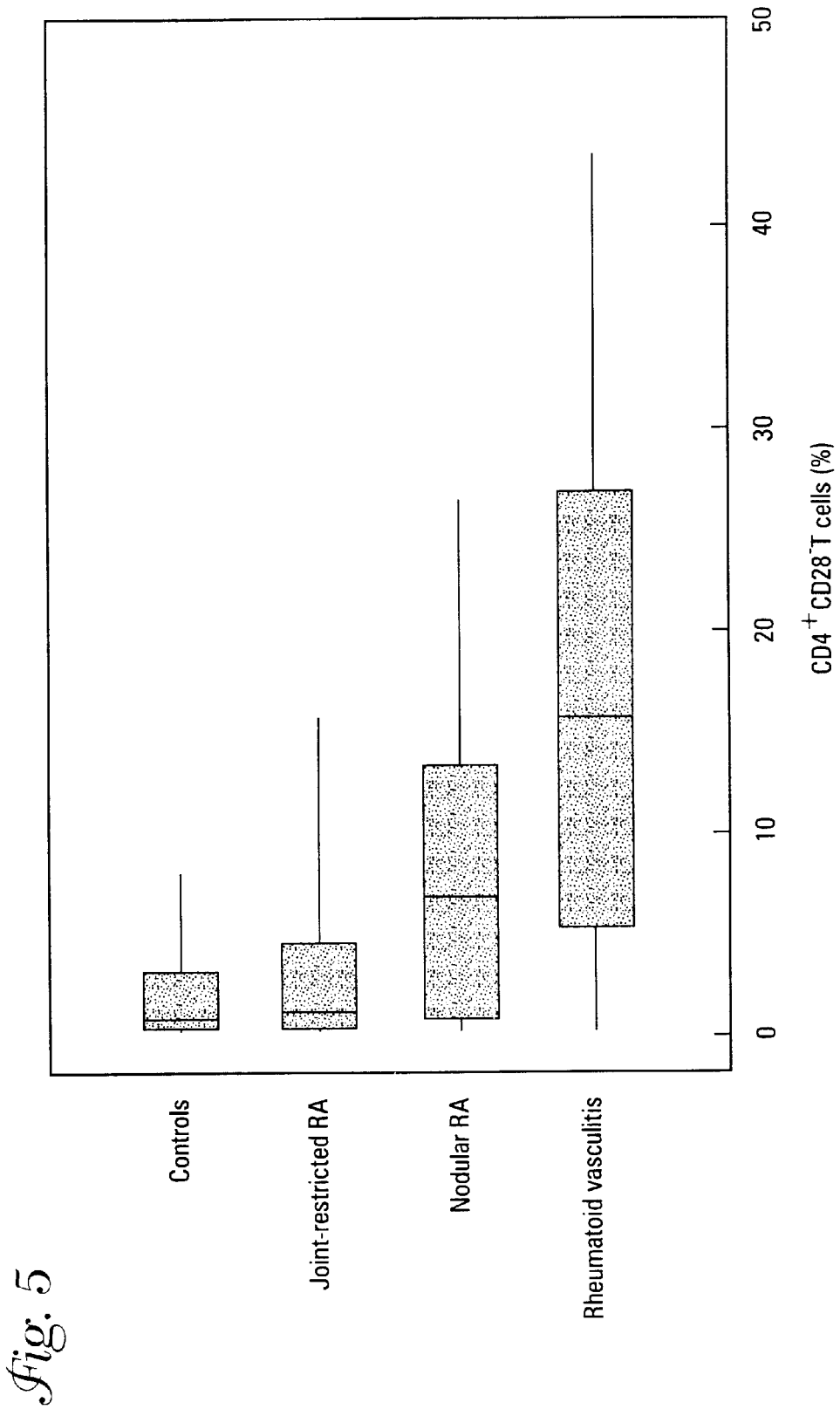
FIG. 5 is a bar graph depicting the correlation between the frequencies of $CD4^+/CD28^{null}$ T cells and extra-articular rheumatoid arthritis. The line corresponds to the median, the box to the $25^{th}$ and $75^{th}$ percentiles, and the whiskers to the $10^{th}$ and $90^{th}$ percentiles.

Several groups have made the observation that RA patients carry clonally expanded T cell populations not only in the synovial compartment, as one would expect, but also in the peripheral T cell repertoire (DerSimonian H, et al., *J Exp Med* 177:1623 (1993); Fitzgerald J E, et al., *J Immunol* 154:3538 (1995); Gonzalez-Quintial R, et al., *J Clin Invest* 97:1335 (1996); Goronzy J J, et al., *J Clin Invest* 94:2068 (1994); Hingorani R, et al., *J Immunol* 156:852 (1996); and Lim A, et al., *Hum Immunol* 48:77 (1996)). Genetic susceptibility for the formation of T cell oligoclonality was suggested by the finding that CD4 T cell clones were present in affected as well as unaffected members of multi-case families with RA (Waase I, et al., *Arthritis Rheum* 39:904 (1996)). The isolation of clonally expanded CD4 T cells from patients with RA has allowed for the phenotypic and functional characterization of these T cells (Schmidt D, et al., *J Clin Invest* 97:2027 (1996)). Expanded CD4 clonotypes were found to be deficient for the expression of the CD28 molecule. Because CD28 has been identified as a key player in T cell costimulation, this finding raised the question whether CD28-deficient CD4 T cells are functionally competent and how, if so, they contribute to RA. CD28-deficient CD4 T cells, as opposed to $CD8^+/CD28^{null}$ T cells, are infrequent in normal individuals. Most normal donors have <1% $CD4^+/CD28^{null}$ T cells (Martens P B, et al., *Arthritis Rheum* 40:1106 (1997)). In contrast, increased frequencies of CD28-deficient CD4 T cells are detected in patients with RA (FIG. 4). Association studies of $CD4^+/CD28^{null}$ T cells in patient cohorts stratified for different disease manifestations showed that the size of the $CD4^+/CD28^{null}$ T cell compartment is closely associated with extra-articular RA (FIG. 5). Patients with RA limited to the joint expressed a median of 1.1% $CD4^+/CD28^{null}$ T cells. In patients with rheumatoid nodules, 7% of the CD4 T cells were CD28-deficient. CD4 T cells lacking CD28 expression were encountered in almost all patients with rheumatoid organ disease. In patients with rheumatoid vasculitis, CD28-deficient T cells accounted for up to 50% of the $CD4^+$ subset. A role of $CD4^+/CD28^{null}$ T cells in extra-articular aspects of RA is also supported by their distribution pattern. These unusual CD4 T cells are circulating in the blood and are generally encountered in the synovial tissue, but they are not selectively enriched in the synovial compartment (Rittner H L, et al., *Mol Med* 3:452 (1997)).

It could be argued that the emergence of $CD4^+/CD28^{null}$ T cells in RA patients is a consequence of chronic persistent inflammation. Several lines of evidence do not support this interpretation. In the normal population, "carriers" for $CD4^+/CD28^{null}$ T cells can be found, although they are infrequent. In these normal individuals, as well as in RA patients, the proportion of $CD4^+/CD28^{null}$ T cells remains constant over several years. No influence of disease duration or therapy on the expansion of the $CD4^+/CD28^{null}$ compartment has been detected. Rather, the expression of CD28-deficient CD4 T cells is a hallmark of early and untreated disease. Most importantly, indirect evidence suggests genetic control of $CD4^+/CD28^{null}$ T cells. A study evaluating the presence of $CD4^+/CD28^{null}$ T cells in monozygotic and dizygotic twins and in spouse pairs revealed a high concordance in the monozygotic twin pairs but a lack of correlation in the spouse pairs. It is proposed herein that the generation of $CD4^+/CD28^{null}$ T cells is at least partially influenced by inherited factors.

The molecular basis of CD28 deficiency has been addressed as the loss of this important costimulatory molecule and may provide clues as to how these cells emerge. The expression of CD28 on the cell surface has been correlated with the presence of two DNA binding proteins that bind to sequence motifs within the minimal promoter of the CD28 gene (Vallejo A N, et al., *J Biol Chem* 273:8119–29 (1998)). These regulatory proteins are absent in $CD4^+/CD28^{null}$ T cells, providing a tool to approach the mechanisms controlling CD28 expression. So far, besides RA, one more factor has been associated with the loss of these gene specific regulatory proteins, namely advanced age of the donor.

As outlined, the presence of CD4 T cells defective for CD28 expression correlated with the presence of extra-articular disease. Available data indicate that $CD4^+/CD28^{null}$ T cells differ from traditional $CD4^+$ helper T cells in several aspects. $CD4^+/CD28^{null}$ T cells are dependent on costimulatory signals provided by accessory cells to be fully activated (Park W, et al., *Eur J Immunol* 27:1082 (1997)). However, blocking studies with CTLA-4-Ig fusion protein have demonstrated that costimulation does not involve a CD28/CTLA-4-CD80/CD86 interaction. Also, costimulation enhances the proliferative response and upregulates IL-2R expression but has no effect on the cytokine production. Compared to CD4+/CD28+ T cells, CD28-deficient CD4+ T cell clones produce higher amounts of IFN-γ but similar amounts of IL-2 and IL-4. IFN-γ production is not enhanced by accessory cells, suggesting that the secretion of IFN-γ by CD4+/CD28$^{null}$ T cells is independent of costimulatory mechanisms. As a second important difference to traditional helper cells, CD4+/CD28$^{null}$ T cells lack the expression of CD40 ligand (CD40L) and fail to provide helper cell signals for B cell differentiation and immunoglobulin production (Weyand C M, et al., *Mech Age Develop* In press (1998)). In contrast, they have been found to transcribe and produce perforin, a molecule tightly linked with cytotoxic capability (Namekawa T, et al., *Arthritis Rheum*. 41(12):2108–16 (1998)). Cytotoxic activity of CD4+/CD28$^{null}$ T cells has been demonstrated in vitro. An inverse relationship of CD40L and perforin expression has also been shown for synovial CD4 T cells, supporting the model that synovial CD4 T cells fall into phenotypically and functionally distinct categories. The cytolytic capability of CD4+/CD28$^{null}$ T cells raises the question as to which target cells are attacked by these unusual lymphocytes in vivo. This is determined by the antigen-specificity of these expanded T cells. In vitro studies have provided evidence that the antigen of interest might be an autoantigen presented by adherent cells but not by B cells (Chapman A, et al., *J Immunol* 157:4771 (1996); and Schmidt D, et al., *J Clin Invest* 97:2027 (1996)). The number of antigens recognized appears to be restricted; CD28$^{null}$ expanded clonotypes isolated from different RA patients were found to express identical amino acid sequences in the TCR β-chain (Schmidt D, et al., *Mol Med* 2:608 (1996)). Because of the particular association of CD4+/CD28$^{null}$ T cells with extra-articular disease and because such disease manifestations in RA have been related to vascular complications, it seems prudent to evaluate the interaction between CD4+/CD28$^{null}$ T cells and endothelial cells.

In summary, patients with extra-articular RA express CD4 T cells with an unusual phenotype and an unusual functional profile. CD4+/CD28$^{null}$ T cells undergo clonal expansion in vivo, persist over many years, do not transcribe CD40L and have cytotoxic capability (Table 6). They may occupy up to one-half of the CD4 compartment and are characterized by their ability to secrete high amounts of IFN-γ in the absence of costimulatory signals. The emergence of these T cells may be under genetic control, as suggested by the high rate of concordance in the size of the CD4+/CD28$^{null}$ T cell compartment in monozygotic twins.

TABLE 6

Characteristics of CD4+/CD28$^{null}$ T cells in RA

Oligoclonality
Expanded in early disease
Persistence over years
No correlation with disease duration or therapy
Infiltration into synovial lesions
Costimulation independent of CD80/CD86
Production of high concentrations of IFN-γ
Autoreactivity in response to adherent cells
Impaired apoptosis with overexpression of bcl-2
Transcriptional block of the CD28 gene due to a deficiency of two gene-specific transcription factors 1. Cell Surface Staining to Determine CD4+/CD28$^{null}$ Cell Frequency PBMC were isolated from the patient and stained (20 minutes at 4° C.) with a combination of two of the following monoclonal antibodies, anti-CD3 (fluorescein isothiocyanate [FITC]-conjugated), anti-CD4 (peridinin chlorophyll protein [PerCP]-conjugated), anti-CD8 PerCP-conjugated (all from Becton Dickinson, San Jose, Calif.), and anti-CD28 FITC-conjugated (Pharmigen, San Diego, Calif.), and analyzed on a FACS Calibur flow cytometer (Becton Dickinson) to determine the frequencies of CD3+CD4+, CD3+CD8+, and CD4+CD28$^{null}$ T cells. Analysis was performed using WinMIDI software (Joseph Trotter, Scripps Research Institute, La Jolla, Calif.).

2. Flow Cytometric Analysis

Twenty thousand events were analyzed using WinMDI software. A tight light scatter region was drawn to include only viable lymphocytes. CD3+CD4+, CD3+CD8+, CD4+CD28+, CD4+CD28$^{null}$ cells were analyzed for their expression of the cytokines of interest. In all experiments, less than 1% of the cells were positive for the isotype controls, demonstrating a very high staining specificity.

Example 9

Variants of RA Defined by Distinct Patterns of Synovial Inflammation

The primary manifestations of RA are found in the synovial membrane of diarthroidal joints. Histopathologic changes include dense infiltrates of mononuclear cells, neoangiogenesis, and hypertrophy and hyperplasia of synoviocytes. Although it is reasonable to assume that all of the different cell types accumulated in the synovial lesions have a role in the pathologic events, the exact contributions of monocytes, T cells, B cells, and resident synovial cells have not been delineated. Keeping in mind that more than one form of RA may exist creates the challenging question whether the contribution of these different cells to the inflammation may be variable. Heterogeneity of rheumatoid synovitis is certainly encountered as far as the histomorphologic appearance of the disease lesions is concerned. Pathologic findings in synovial tissues have so far not been helpful in guiding clinical management. While most other fields in medicine have used more sophisticated approaches in tissue diagnostics, this has not been the case for rheumatology. RA has remained primarily a clinical diagnosis (Arnett F C, et al., *Arthritis Rheum* 31:315 (1988)). It is possible that the presumed lack of information gained from histomorphologic inspection of synovial lesions relates to the misleading expectations that RA is a narrowly defined category that should produce a unique pathomorphology.

Evidence for heterogeneity of rheumatoid synovitis comes from the data presented herein correlating the microanatomy of the inflamed synovial membrane with tissue cytokine patterns. T cells, B cells, and macrophages can acquire a highly specialized topography in the synovium. These cells usually accumulate in the sublining stroma and are either arranged as diffuse infiltrates or are organized into structures reminiscent of secondary lymphoid tissues. One of the remarkable structures found in rheumatoid synovitis is T cell-B cell aggregates, which form germinal centers (GCs). Synovial GCs include all of the necessary cellular components and the defined topographical arrangement required for GC reactions to occur. Specifically, networks of CD23+ follicular dendritic cells are localized in the centers of T cell-B cell follicles. These networks are populated by IgD-B cells and surrounded by CD4 T cells, some of which express CD40L (Wagner U G, et al., *J Immunol*. 161:6390–7 (1998)). The formation of GCs in the synovial membrane, a primarily non-lymphoid tissue, is a highly significant event that emphasizes the role of the immune system in this disease and stresses the critical contribution of antigen and antigen recognition in pathology. It is, however, important to note that only a subset of patients forms such synovial GCs. Histopathologic patterns of rheumatoid synovitis were examined in a series of biopsies collected from patients with active arthritis (Klimiuk P A, et al., *Am J Pathol* 151:1311 (1997)). In this case series, three distinct patterns emerged. One-third of all samples contained GC-like follicles. In a slightly higher proportion of samples, T cells, B cells, and CD68+ macrophages lacked a specialized microanatomical formation, but formed a diffuse infiltrate. A third pattern of synovitis was encountered in the minority of samples. This granulomatous pattern was characterized by necrotic centers lined by a collar of epithelioid histiocytes, with or without giant cells. Typically, marked angiogenesis was found external to the palisade of histiocytes in areas with mixed infiltrates composed of lymphocytes, plasma cells, and macrophages. It is important to note that in this study, follicular synovitis and granulomatous necrobiosis did not co-occur. Rather, patients appeared to either organize the synovial lesions into follicular or granulomatous patterns.

To examine the relevance of microanatomical arrangements for the inflammatory process, tissue cytokine profiles were determined. IFN-γ and IL-4 were chosen as the marker cytokines for $T_H1$ and $T_H2$ helper cells. IFN-γ and IL-4 were present in low abundance in tissues with diffuse synovitis. In follicular synovitis IFN-γ was transcribed at intermediate levels but IL-4 was distinctly absent. Granulomatous synovitis was associated with the highest tissue concentrations for both IFN-γ and IL-4. The production of the macrophage products, IL-1β and TNF-α, correlated closely with the amount of IFN-γ mRNA. Abundant transcription of both macrophage products was a feature of granulomatous synovitis. Moderate levels were detected in follicular synovitis, and tissues with diffuse synovitis produced low concentrations of IL-1β and TNF-α. The subdued production of the T cell products, IFN-γ and IL-4, as well as the macrophage products, IL-1β and TNF-α, in samples with diffuse synovitis could not be explained by the action of the anti-inflammatory cytokines, IL-10 and TGF-β1. High transcription of the IL-10 gene was typical for follicular disease. TCF-β1 was most abundant in tissue extracts from follicular synovitis, but it was also present in high amounts in synovial biopsies with granuloma formation.

Taken together, reproducible patterns of organization of inflammatory cells in the synovial infiltrates were distinguished. The topography of the infiltrates correlated with distinct profiles of tissue cytokines, indicating that RA is not always characterized by a predominant $T_H1$ response as previously reported (Simon A K, et al., *Proc Natl Acad Sci USA* 91:8562 (1994)) but that different cytokine pathways underlie the synovial inflammation (Table 7). RA is not a consequence of an immunodeviation of the cellular cytokine response as has been postulated for other autoimmune diseases (Finkelman F D, *J Exp Med* 182:279 (1995)), but it includes different response patterns, each of which may be genetically determined and may have different clinical implications.

Support for clinical relevance of the described patterns in organization and functional commitment of the infiltrating cells came from an analysis of disease manifestations and outcome. The best predictor for diffuse synovitis was a lack of RF production, a disease type previously associated with the genotype HLA-DRB1*01 or characterized by the absence of disease-associated HLA-DRB1 alleles. Patients with this form of RA synovitis often only require non-steroidal anti-inflammatory drugs and infrequently receive more aggressive treatment. Granulomatous synovitis was encountered in patients with extra-articular spreading and nodule formation. Comparison among different joints from the same patient have shown that a pattern is characteristic for each patient and that the synovial lesions in different joints display identical organizations.

The phenotypic dissection of rheumatoid synovitis requires the reevaluation of the concept that has recently been proposed as the major mechanism leading to tissue destructive inflammation. Immune deviation has been defined as an aberrant commitment to an immune pathway in response to a given antigen. Elegant studies in model systems such as leishmania major infection have provided evidence that, dependent on the genetic background of the host, an immune response to a given antigen can take different directions, thereby determining whether the disease resolves or progresses (Heinzel F P, et al., *J Exp Med* 169:59 (1989)). It has been suggested that patients with RA display a similar immune deviation with a bias towards $T_H1$ responses (Simon A K, et al., *Proc Natl Acad Sci USA* 91:8562 (1994)). Consequently, it has been proposed to use IL-4 and IL-10 as novel therapeutic agents in the attempt to restore $T_H2$ responsiveness and suppress dominant $T_H1$ responses (Isomaki P, et al., *Arthritis Rheum* 39:386 (1996); van Roon J A, et al., *Arthritis Rheum* 39:829 (1996); and Walmsley M, et al., *Arthritis Rheum* 39:495 (1996)). The data herein describing three different tissue cytokine profiles raise doubt that RA can be considered a single entity caused by overproduction of $T_H1$ cytokines. This model may apply to only a subset of individuals clinically classified as RA. The proposed treatment approaches with IL-4 and IL-10 illustrate the shortcomings of a disease model of RA that does not adequately consider phenotypic and genotypic variability. IL-4 and IL-10 might be beneficial in some but not all forms of the disease. Ignoring the heterogeneity of the disease process and its clinical spectrum could represent a major limitation in treatment trials.

TABLE 7

Tissue cytokine patterns in subtypes of rheumatoid synovitis

| Cytokine | Diffuse synovitis | Follicular synovitis | Granulomatous synovitis |
|---|---|---|---|
| IFN-γ | + | ++ | +++ |
| IL-4 | + | − | +++ |
| IL-1β | + | ++ | +++ |
| TNF-α | + | ++ | +++ |
| IL-10 | + | +++ | + |
| TGF-β1 | ++ | +++ | +++ |

Example 10

Evaluating RA

Figure 6:
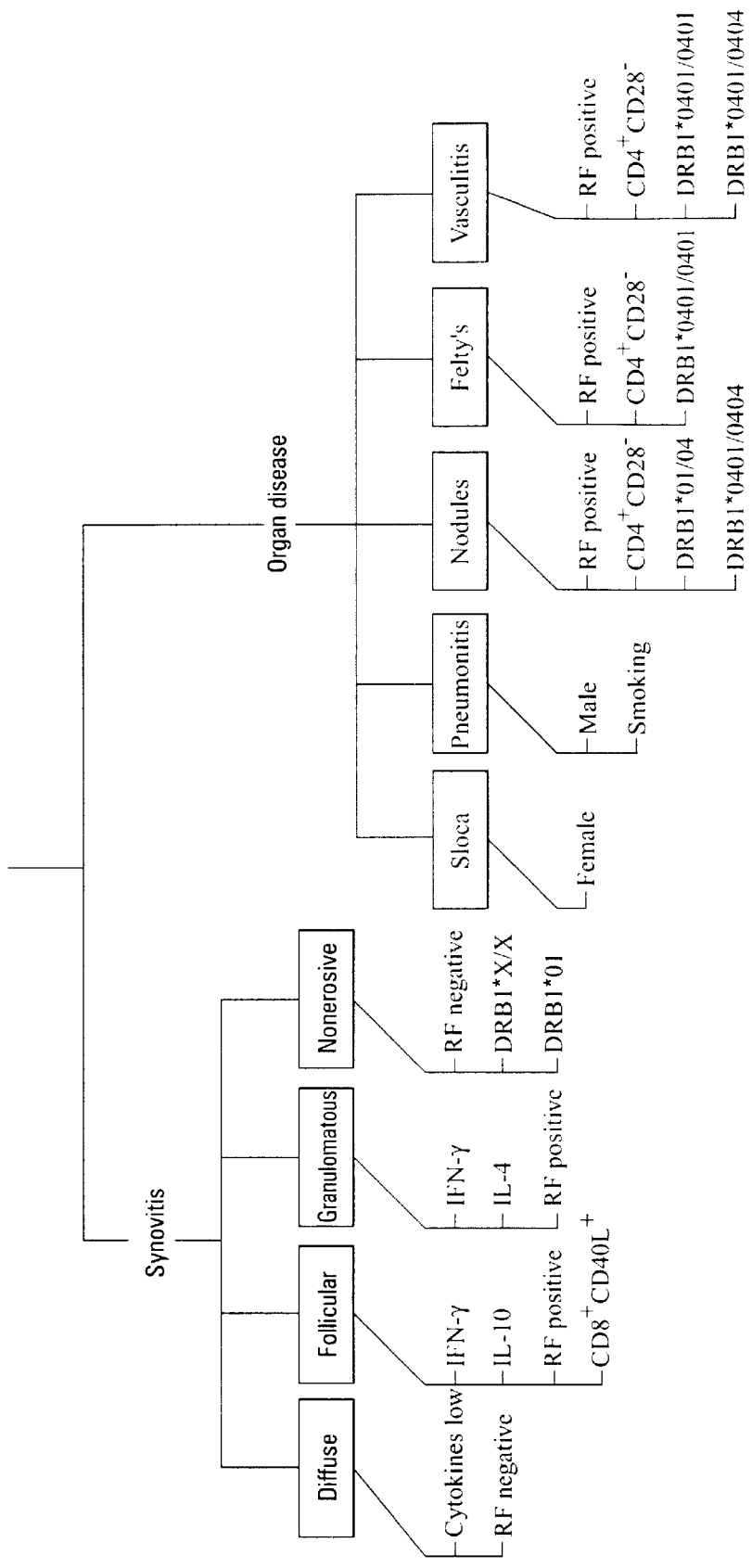
FIG. 6 is a chart depicting possible genetic factors of disease heterogeneity in rheumatoid arthritis.

RA can be subsetted into different phenotypes that correlate with the inheritance of distinct combinations of disease-risk genes (FIG. 6). Combinations of HLA-DRB1 alleles and particular polymorphisms of HLA-DRB1 genes are useful in dissecting patients with rheumatoid organ disease, the most feared complication of RA. Contribution from a distinct genetic system to rheumatoid organ disease is suggested by the accumulation of unusual lymphocytes in patients suffering from complications of RA. CD4 T cells characterized by the deficiency of CD28, a major co-stimulatory molecule, expand to high frequencies in patients with extra-articular RA. $CD4^+/CD28^{null}$ T cells are functionally active, produce high amounts of IFN-γ and use a yet unknown alternate costimulatory pathway. These cells typically undergo clonal proliferation in vivo and infiltrate into the inflammatory lesions. Concordance for the expansion of this unusual lymphocyte subset in monozygotic twins lends support to a genetic control of their emergence. CD4$^+$/CD28$^{null}$ T cells accumulate in RA patients independent of HLA-DR polymorphisms. Therefore, genes regulating their generation might represent novel RA risk genes.

Additional RA risk genes can include genes involved in regulating cytokine pathways. Analysis of tissue cytokine profiles in rheumatoid synovitis demonstrated three distinct patterns of microanatomical organization of the inflammatory infiltrates and, more importantly, a close correlation of lymphoid structures and cytokine networks. RA does not simply arise from immune deviation; at least three different cytokine pathways are involved in RA synovitis. Recognition of this heterogeneity is essential in trying to identify the molecular mechanisms that induce either diffuse, follicular, or granulomatous synovitis.

Accepting the model that more than one genotype can be associated with RA has enormous implications. Genomic searches trying to identify shared denominators among affected individuals rely heavily on the definition of disease. If individuals with too many different types of disease are compared, the chance of identifying disease risk genes is low. Similar considerations apply to studies trying to identify disease instigators. If disease processes are heterogeneous and patients with different variants of RA are studied, it might be impossible to identify a causative agent present in all or most of them. All of these approaches would have a much higher power if study cohorts could be identified that represented distinct disease entities. Focusing on a single variant of RA would enhance the chance of identifying molecular abnormalities, genetic risk factors, and potential infectious agents involved in RA pathogenesis. From a clinical point of view, the dissection of phenotypic/genotypic variants of RA is critical for further exploration of new and more selective therapeutic avenues. The therapeutic benefit of intervention might depend on the ability to target the appropriate patient subset.

The cytokine profile within synovial tissue, the patient's HLA genotype, and the patient's frequency of CD4$^+$/CD28$^{null}$ T cells was used to determine the patient's predisposition to develop severe disease. Subcutaneous nodularity was used as an indicator of disease severity. Tissue type was independent of HLA-DRB1 genotype and CD4$^+$/CD28$^{null}$ T cells counts were independent of HLA-DRB1 genotype (Table 8). Granulomatous disease predicts nodularity independent of HLA-DRB1 genotype and CD4$^+$/CD28$^{null}$ T cells counts. With respect to diffuse disease, CD4$^+$/CD28$^{null}$ T cell counts were a better predictor for nodular disease than a HLA-DRB1 homozygous positive genotype.

TABLE 8

Evaluating RA patients for disease severity.

| Tissue cytokines | | | |
|---|---|---|---|
| IL-4 | low | low | high |
| IL-10 | low | high | low |
| IFN-γ | low | high | high |
| Corresponding histology | diffuse | follicular | granulomatous |
| Patients (number) | 31 | 12 | 6 |
| RA-associated HLA-DRBI *04 allele | 20 (65%) | 7 (58%) | 4 (66%) |

TABLE 8-continued

Evaluating RA patients for disease severity.

| | | | |
|---|---|---|---|
| Two RA-associated HLA-DRB1 alleles (Double-dose) | 8 (25%) | 3 (25%) | 0 (0%) |
| Nodularity (%) | 9 (29%) | 2 (17%) | 5 (84%) |
| % of nodular patient being double-dose (sensitivity) | 2 (22%) | 1 (50%) | 0% |
| % of double-dose patients being nodular | 2 (25%) | 1 (33%) | N/A |
| CD4+ CD28– data available | 7 | 3 | 3 |
| Number of patients having high CD4$^+$/CD28$^{null}$ counts | 3 | 2 | 2 |
| Number of patients being nodular | 2 | 1 | 3 |
| % of patients having high high CD4CD4$^+$/CD28$^{nullnull}$ counts counts that that are are nodularnodular | 2/3x | (66%)(66%) (50%)(50%) | 11 100%100% |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for evaluating a rheumatoid arthritis condition in a patient, said method comprising:
   a) determining the level of one or more cytokines within a sample from said patient, wherein said one or more cytokines is selected from the group consisting of interleukin-1 beta, interleukin-4, interleukin-10, interferon-gamma, tumor necrosis factor-alpha, and transforming growth factor-beta,
   b) comparing said level of said one or more cytokines to one or more reference levels to obtain information about said rheumatoid arthritis condition, and
   c) classifying said rheumatoid arthritis condition as a diffuse, follicular, or granulomatous condition based on said information.

2. The method of claim 1, wherein said sample comprises a tissue biopsy.

3. The method of claim 2, wherein said tissue biopsy comprises a synovial tissue biopsy.

4. The method of claim 1, wherein said one or more reference levels comprises information about the median level of said one or more cytokines found in tissue samples.

5. The method of claim 4, wherein said tissue samples are from patients having a diffuse rheumatoid arthritis condition.

6. The method of claim 4, wherein said tissue samples are from patients having a follicular rheumatoid arthritis condition.

7. The method of claim 4, wherein said tissue samples are from patients having a granulomatous rheumatoid arthritis condition.

8. The method of claim 4, wherein said tissue samples are from healthy individuals.

9. The method of claim 4, wherein said tissue samples are from patients having subcutaneous nodules.

10. The method of claim 4, wherein said tissue samples are from patients having extra-articular involvement.

11. The method of claim 4, wherein said tissue samples are from patients having major joint destruction.

12. A kit for providing information about a rheumatoid arthritis condition in a patient, said kit comprising:
   a) one or more binding pair members, wherein each of said one or more binding pair members has specific binding affinity for a cytokine such that the level of said cytokine within a sample from said patient is determinable, wherein said cytokine is selected from the group consisting of interleukin-1 beta, interleukin-4, interleukin-10, interferon-gamma, tumor necrosis factor-alpha, and transforming growth factor-beta; and
   b) a reference chart, wherein said reference chart contains information about one or more cytokines selected from the group consisting of interleukin-1 beta, interleukin-4, interleukin-10, interferon-gamma, tumor necrosis factor-alpha, and transforming growth factor-beta such that an indication of the diffuse, follicular, or granulomatous nature of said rheumatoid arthritis condition is determinable based on one or more cytokine levels within said sample.

13. The kit of claim 12, wherein at least one of said one or more binding pair members is an antibody.

14. The kit of claim 12, wherein said sample comprises a tissue biopsy.

15. The kit of claim 12, wherein said sample comprises a synovial tissue biopsy.

16. The kit of claim 12, wherein said reference chart comprises information about the median level of said one or more cytokines found in tissue samples.

17. The kit of claim 16, wherein said tissue samples are from patients having a diffuse rheumatoid arthritis condition.

18. The kit of claim 16, wherein said tissue samples are from patients having a follicular rheumatoid arthritis condition.

19. The kit of claim 16, wherein said tissue samples are from patients having a granulomatous rheumatoid arthritis condition.

20. The kit of claim 16, wherein said tissue samples are from healthy individuals.

21. The kit of claim 16, wherein said tissue samples are from patients having subcutaneous nodules.

22. The kit of claim 16, wherein said tissue samples are from patients having extra-articular involvement.

23. The kit of claim 16, wherein said tissue samples are from patients having major joint destruction.

24. A method for evaluating a rheumatoid arthritis condition in a patient, said method comprising:
   a) determining the level of one or more cytokines within a sample from said patient, wherein each of said one or more cytokines is selected from the group consisting of interleukin-1 beta, interleukin-4, interleukin-10, interferon-gamma, tumor necrosis factor-alpha, and transforming growth factor-beta,
   b) comparing said level to one or more reference levels to obtain information about said rheumatoid arthritis condition, and
   c) classifying said rheumatoid arthritis condition as not being a diffuse, follicular, or granulomatous condition based on said information.

25. The method of claim 24, wherein said sample comprises a tissue biopsy.

26. The method of claim 25, wherein said tissue biopsy comprises a synovial tissue biopsy.

27. The method of claim 24, wherein said one or more reference levels comprises information about the median level of said one or more cytokines found in tissue samples.

28. The method of claim 27, wherein said tissue samples are from patients having a diffuse rheumatoid arthritis condition.

29. The method of claim 27, wherein said tissue samples are from patients having a follicular rheumatoid arthritis condition.

30. The method of claim 27, wherein said tissue samples are from patients having a granulomatous rheumatoid arthritis condition.

31. The method of claim 27, wherein said tissue samples are from healthy individuals.

32. The method of claim 27, wherein said tissue samples are from patients having subcutaneous nodules.

33. The method of claim 27, wherein said tissue samples are from patients having extra-articular involvement.

34. The method of claim 27, wherein said tissue samples are from patients having major joint destruction.

* * * * *